United States Patent
Tsukamoto et al.

(10) Patent No.: US 11,149,001 B2
(45) Date of Patent: Oct. 19, 2021

(54) METHOD FOR PRODUCING ε-CAPROLACTAM

(71) Applicant: TORAY INDUSTRIES, INC., Tokyo (JP)

(72) Inventors: Daijiro Tsukamoto, Kamakura (JP); Masateru Ito, Kamakura (JP); Katsushige Yamada, Kamakura (JP); Masato Akahira, Nagoya (JP); Daisuke Yamamoto, Nagoya (JP); Koji Yamauchi, Nagoya (JP)

(73) Assignee: TORAY INDUSTRIES, INC., Tokyo (JP)

( * ) Notice: Subject to any disclaimer, the term of this patent is extended or adjusted under 35 U.S.C. 154(b) by 60 days.

(21) Appl. No.: 16/466,230

(22) PCT Filed: Dec. 5, 2017

(86) PCT No.: PCT/JP2017/043539
§ 371 (c)(1),
(2) Date: Jun. 3, 2019

(87) PCT Pub. No.: WO2018/105572
PCT Pub. Date: Jun. 14, 2018

(65) Prior Publication Data
US 2020/0062704 A1   Feb. 27, 2020

(30) Foreign Application Priority Data

Dec. 6, 2016 (JP) .............................. JP2016-236624
Mar. 3, 2017 (JP) .............................. JP2017-040208

(51) Int. Cl.
| | | |
|---|---|---|
| *C07D 201/00* | (2006.01) | |
| *C07D 223/00* | (2006.01) | |
| *C07C 255/00* | (2006.01) | |
| *C07D 201/08* | (2006.01) | |
| *C07D 223/10* | (2006.01) | |

(52) U.S. Cl.
CPC ......... *C07D 201/08* (2013.01); *C07D 223/10* (2013.01)

(58) Field of Classification Search
CPC .... C07D 223/10; C07D 201/08; C07B 61/00; B01J 23/648; B01J 23/847; C07C 255/19
See application file for complete search history.

(56) References Cited

U.S. PATENT DOCUMENTS 10,196,352 B2   2/2019 Ito et al.

FOREIGN PATENT DOCUMENTS

| GB | 494 236 | * 10/1938 |
| WO | WO 01/77068 A2 | 10/2001 |
| WO | WO 2012/141997 A1 | 10/2012 |
| WO | WO 2013/126250 A1 | 8/2013 |
| WO | WO 2016/068108 A1 | 5/2016 |

OTHER PUBLICATIONS

Extended European Search Report for European Application No. 17879609.0, dated Jun. 25, 2020.

* cited by examiner

*Primary Examiner* — Sikarl A Witherspoon
(74) *Attorney, Agent, or Firm* — Birch, Stewart, Kolasch & Birch, LLP

(57) ABSTRACT

A method produces ε-caprolactam through adipamide as an intermediate, and characteristically includes a lactamization step of reacting adipamide, formed from a material compound, with hydrogen and ammonia in the presence of a catalyst containing: a metal oxide mainly containing an oxide(s) of one or more metallic elements selected from the group consisting of metallic elements of group 5 and groups 7 to 14 in the 4th to 6th periods of the periodic table; and a metal and/or a metal compound having a hydrogenation ability.

4 Claims, No Drawings

METHOD FOR PRODUCING ε-CAPROLACTAM

TECHNICAL FIELD

The present invention relates to a method of producing ε-caprolactam, which can be used as a material of polyamide.

BACKGROUND ART

ε-Caprolactam is an important chemical material that can be used as a material for polyamides and the like, and is industrially formed worldwide. It is mostly used as a material for Nylon 6, which is a polyamide. As an industrial production method of ε-caprolactam, a production method using the Beckmann rearrangement reaction with fuming sulfuric acid from cyclohexanone oxime has been widely employed. This production method uses crude oil as a starting material. From the viewpoint of possible depletion of fossil resources in the future, and the problem of global warming caused by greenhouse gases emitted during mining and use of fossil resources, development of methods of producing ε-caprolactam using alternative materials has been demanded. In particular, methods of producing ε-caprolactam from compounds derived from biomass resources, which are renewable resources, are attracting attention.

As a specific example of a method of producing ε-caprolactam from a compound derived from biomass resources, Patent Document 1 discloses a method of producing ε-caprolactam by reacting adipic acid, which is a compound derived from biomass resources, with hydrogen and ammonia in the presence of a catalyst.

Patent Document 2 discloses a method of producing ε-caprolactam by reacting muconic acid, which is a compound derived from biomass resources, with hydrogen and ammonia in the presence of a catalyst.

Patent Document 3 discloses a method of producing δ-caprolactam by reacting α-hydromuconic acid, 3-hydroxyadipic acid, or 3-hydroxyadipic acid-3,6-lactone, which is a compound derived from biomass resources, with hydrogen and ammonia in the presence of a catalyst.

Patent Documents 1 to 3 disclose that adipamide is formed as an intermediate during the processes of production of ε-caprolactam from the compounds derived from biomass resources.

PRIOR ART DOCUMENTS

Patent Documents

Patent Document 1: WO 2013/126250
Patent Document 2: WO 2012/141997
Patent Document 3: WO 2016/68108

SUMMARY OF THE INVENTION

Problems to be Solved by the Invention

The present inventors found, as a new technical problem, that production of ε-caprolactam from compounds such as adipic acid according to the above methods results in insufficient ε-caprolactam selectivities because of remarkable formation of by-products during the process of conversion of adipamide as an intermediate to ε-caprolactam, which by-products do not contribute to the formation of ε-caprolactam from adipamide.

Means for Solving the Problems

As a result of intensive study for solving the above problem, the present inventors discovered that side reactions from adipamide can be suppressed, and that the ε-caprolactam selectivity can thus be increased, by using a catalyst containing: a metal oxide mainly containing an oxide(s) of one or more metallic elements selected from the group consisting of metallic elements of group 5 and groups 7 to 14 in the 4th to 6th periods of the periodic table; and a metal and/or a metal compound having a hydrogenation ability; thereby completing the present invention.

That is, the present invention is constituted by the following (1) to (12).

(1) A method of producing ε-caprolactam through adipamide as an intermediate, the method comprising a lactamization step of reacting adipamide, formed from a material compound, with hydrogen and ammonia in the presence of a catalyst, wherein the catalyst comprises a metal oxide mainly containing an oxide(s) of one or more metallic elements selected from the group consisting of metallic elements of group 5 and groups 7 to 14 in the 4th to 6th periods of the periodic table; and a metal and/or a metal compound having a hydrogenation ability.

(2) The method according to (1), wherein the material compound is a carboxylic acid represented by the following General Formula (I) or (II):

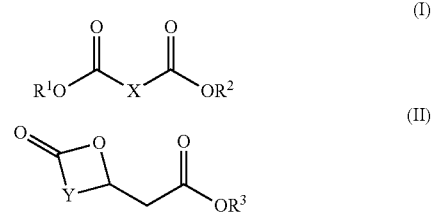

[wherein in Formula (I) and Formula (II), $R^1$, $R^2$, and $R^3$ each independently represent a hydrogen atom (H) or an alkyl group having 1 to 6 carbon atoms; in Formula (I), X represents —$CH_2$—$CH_2$—$CH_2$—$CH_2$—, —$CH_2$—$CH_2$—CH=CH—, —$CH_2$—CH=CH—$CH_2$—, —CH=CH—CH=CH—, —$CH_2$—$CH_2$—$CH_2$—CH(OH)—, —$CH_2$—$CH_2$—C(OH)H—$CH_2$—, —CH=CH—C(OH)H—$CH_2$—, —C(OH)H—$CH_2$—CH=CH—, or —$CH_2$—CH=CH—CH(OH)—; and, in Formula (II), Y represents —$CH_2$—$CH_2$— or —CH=CH—],
or a salt or an ester thereof, or a mixture thereof.

(3) The method according to (1) or (2), wherein the material compound is one or more compounds selected from the following group of compounds:

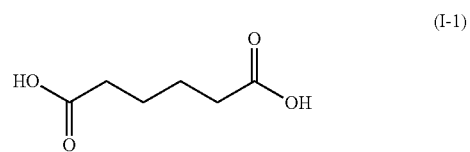

(I-1)

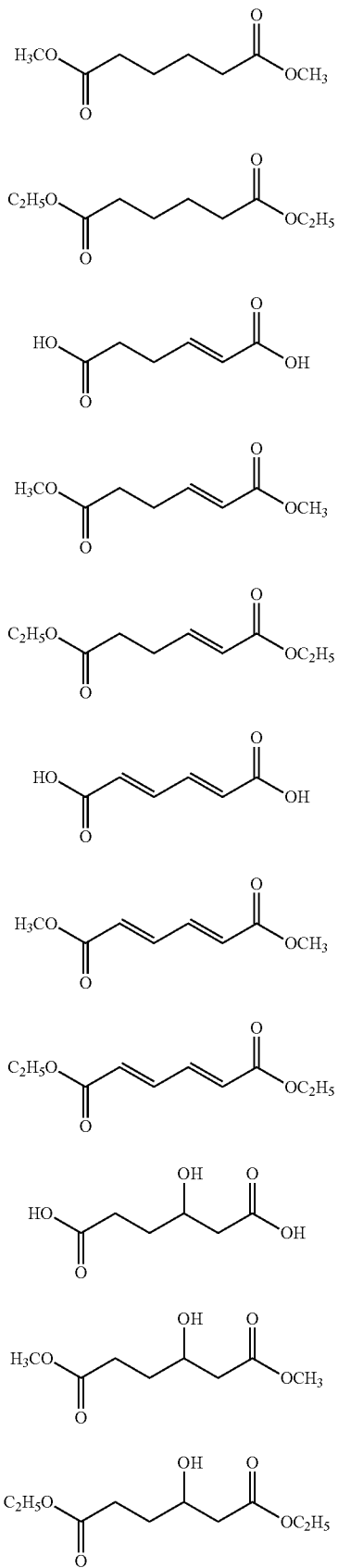
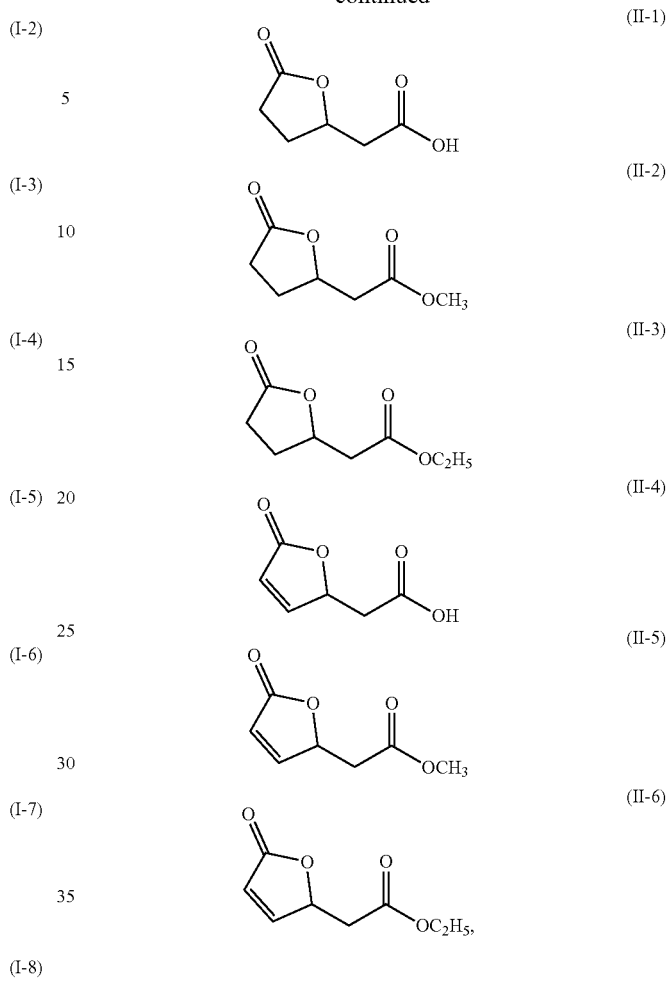

or a salt(s) thereof, or a mixture thereof.

(4) The method according to any one of (1) to (3), wherein the material compound is one or more carboxylic acids selected from the group consisting of adipic acid, muconic acid, 3-hydroxyadipic acid, α-hydromuconic acid, 3-hydroxyadipic acid-3,6-lactone, and muconolactone, or a salt (s) thereof, or a mixture thereof.

(5) The method according to any one of (1) to (4), wherein the oxide(s) of the metallic element(s) is/are an oxide(s) of one or more metallic elements selected from the group consisting of vanadium, niobium, tantalum, manganese, iron, cobalt, nickel, copper, zinc, gallium, indium, thorium, germanium, tin, and lead.

(6) The method according to any one of (1) to (5), wherein the metal and/or the metal compound having a hydrogenation ability contain(s) one or more transition metal elements selected from the group consisting of palladium, platinum, ruthenium, rhodium, rhenium, nickel, cobalt, iron, iridium, osmium, copper, and chromium.

(7) The method according to any one of (1) to (6), wherein the lactamization step is carried out in the absence of oxygen.

(8) A method of producing 5-cyanovaleramide, the method comprising converting adipamide, formed from a material compound, to 5-cyanovaleramide in the presence of a metal oxide mainly containing an oxide(s) of one or more metallic elements selected from the group consisting of metallic elements of group 5 and groups 7 to 14 in the 4th to 6th periods of the periodic table.

(9) The method according to (8), wherein the material compound is a carboxylic acid represented by the General Formula (I) or (II) recited above in (3), or a salt or an ester thereof, or a mixture thereof.
(10) The method according to (8) or (9), wherein the material compound is one or more compounds selected from the group of compounds shown above in (4), or a salt(s) thereof, or a mixture thereof.
(11) The method according to any one of (8) to (10), wherein the material compound is one or more carboxylic acids selected from the group consisting of adipic acid, muconic acid, 3-hydroxyadipic acid, α-hydromuconic acid, 3-hydroxyadipic acid-3,6-lactone, and muconolactone, or a salt (s) thereof, or a mixture thereof.
(12) The method according to any one of (8) to (11), wherein the oxide(s) of the metallic element(s) is/are an oxide(s) of one or more metallic elements selected from the group consisting of vanadium, niobium, tantalum, manganese, iron, cobalt, nickel, copper, zinc, gallium, indium, thorium, germanium, tin, and lead.

Effect of the Invention

In a method of producing ε-caprolactam through adipamide as an intermediate, the present invention enables production of ε-caprolactam while suppressing side reactions from adipamide and improving the ε-caprolactam selectivity. 5-Cyanovaleramide can also be formed with a high selectivity from adipamide formed from a material compound.

MODE FOR CARRYING OUT THE INVENTION

The present invention is described below in more detail.
[Lactamization Step]
The lactamization step in the present invention is a reaction step for the purpose of production of ε-caprolactam, wherein adipamide formed from a material compound is reacted with hydrogen and ammonia in the presence of a catalyst. This step is characterized in that it shows a high selectivity of ε-caprolactam as described below. Adipamide is an organic compound that is also called 1,6-hexanediamide, hexanedioic acid amide, or butane-1,4-dicarboxamide, and is a linear dicarboxylic acid amide having 6 carbon atoms.
[ε-Caprolactam Selectivity]
In the process of formation of ε-caprolactam from adipamide, intermediates such as 5-cyanovaleramide and 6-aminohexanamide are formed as shown in the following Scheme 1.

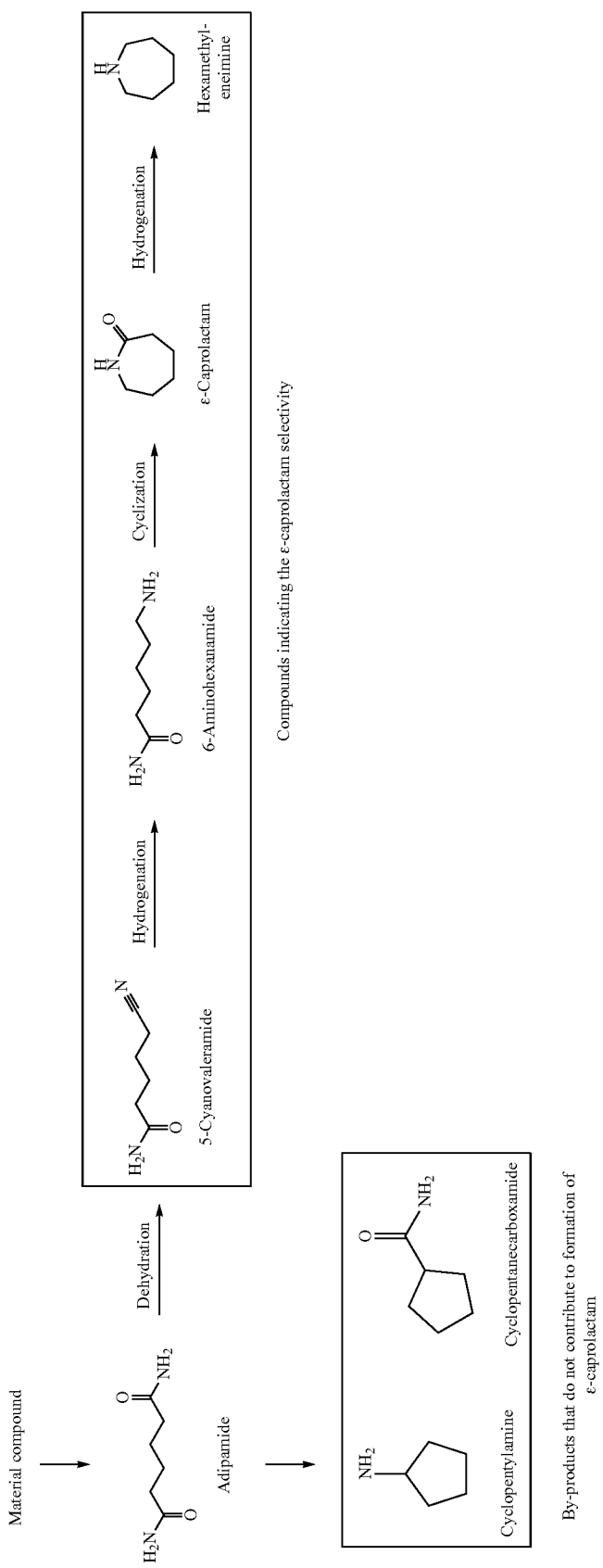

5-Cyanovaleramide is a cyano-containing carboxylic acid amide which is also called 5-cyanopentanamide, wherein one amide group in adipamide is substituted with a cyano group by unimolecular dehydration (U.S. Pat. No. 3,360,541 B). 5-Cyanovaleramide can be converted to 6-aminohexanamide with a yield of 97% in the presence of hydrogen, ammonia, and a hydrogenation catalyst (JP 52-89618 A). By heating 6-aminohexanamide at 300° C. in an industrial white oil, conversion to ε-caprolactam with a yield of 96% can be achieved (JP 7-80837 B). Therefore, even in cases where these intermediates are accumulated in an unreacted state, they may be recovered and subjected again to the lactamization step to form ε-caprolactam. Thus, conversion of adipamide to 5-cyanovaleramide or 6-aminohexanamide can be regarded as a factor that increases the selectivity from adipamide to ε-caprolactam.

On the other hand, in some cases, cyclopentylamine or cyclopentanecarboxamide is formed as a by-product from adipamide. From the descriptions in "ChemSusChem, vol. 6, p. 141-151 (2013)" and "Vollhardt and Schore, Organic Chemistry, 4th ed., p. 972 (Kagaku-Dojin Publishing Co., Inc.; 2004)", this is assumed to be due to abstraction of a hydrogen atom on a nitrogen atom, or a hydrogen atom bound to the carbon atom at the α-position, of adipamide. Since there is no known method of conversion of cyclopentylamine or cyclopentanecarboxamide to ε-caprolactam, formation of these compounds from adipamide can be a factor that decreases the selectivity to ε-caprolactam.

In the lactamization step, formation of hexamethyleneimine occurs due to sequential hydrogen reduction of the ε-caprolactam formed. Since hexamethyleneimine can be converted to ε-caprolactam by air oxidation by a method described in, for example, "Indian Journal of Chemistry, vol. 39B, p. 71-73 (2000)", "Angewandte Chemie International Edition, vol. 55, p 7212-7217 (2016)", or "ACS Catalysis, vol. 1, p. 703-709 (2011)", in cases where hexamethyleneimine is formed in the lactamization step, the hexamethyleneimine can be recovered and air-oxidized to form ε-caprolactam. Therefore, even in cases where hexamethyleneimine is formed in the lactamization step, it can be regarded as a factor that increases the selectivity from adipamide to ε-caprolactam.

Thus, "ε-caprolactam selectivity" in the present description means the total of the selectivities of 5-cyanovaleramide, 6-aminohexanamide, ε-caprolactam, and hexamethyleneimine. As described above, the lactamization step in the present invention is characterized in that it shows a high ε-caprolactam selectivity. As described in the Examples in the present application, the selectivity in the present invention means the ratio of the amount of the product formed to the amount of the material compound consumed.

[Material Compound]

In the present invention, the material compound is not limited as long as it is a compound from which adipamide can be formed by a chemical and/or biological conversion process of not more than several steps. The material compound may be either a compound derived from petroleum or a compound induced from a biomass resource.

More specifically, a carboxylic acid represented by the following General Formula (I) or (II) as described in WO 2013/126250, WO 2012/141997, or WO 2016/68108, or a salt or an ester thereof, is preferred as the material compound in the present invention since adipamide can be formed by its reaction with hydrogen and ammonia.

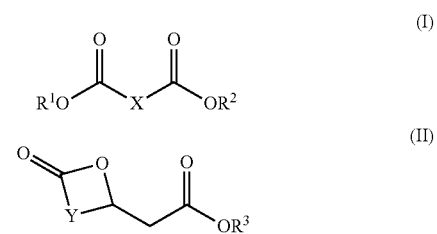

[wherein in Formula (I) and Formula (II), $R^1$, $R^2$, and $R^3$ each independently represent a hydrogen atom (H) or an alkyl group having 1 to 6 carbon atoms; in Formula (I), X represents —$CH_2$—$CH_2$—$CH_2$—$CH_2$—, —$CH_2$—$CH_2$—CH=CH—, —$CH_2$—CH=CH—$CH_2$—, —CH=CH—CH=CH—, —$CH_2$—$CH_2$—$CH_2$—CH(OH)—, —$CH_2$—$CH_2$—C(OH)H—$CH_2$—, —CH=CH—C(OH)H—$CH_2$—, —C(OH)H—$CH_2$—CH=CH—, or —$CH_2$—CH=CH—CH(OH)—; and, in Formula (II), Y represents —$CH_2$—$CH_2$— or —CH=CH—.]

The carboxylic acid represented by General Formula (I) or (II), or the salt or the ester thereof, can be represented also by the following structural formulae.

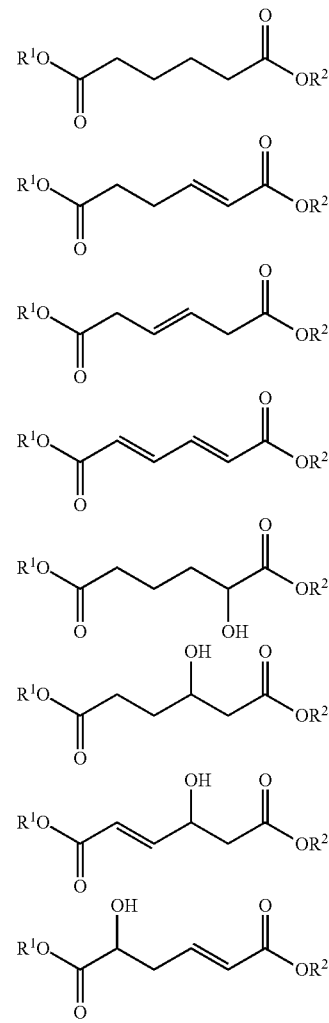

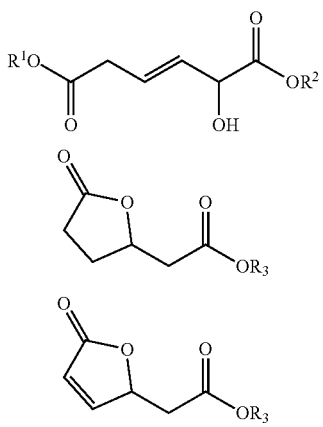

[wherein $R^1$, $R^2$, and $R^3$ each independently represent a hydrogen atom (H) or an alkyl group having 1 to 6 carbon atoms.]

Among the above compounds, from the viewpoint of availability of the material and simplicity of the synthesis, compounds represented by the following Formula (I-1) to Formula (I-12) and Formula (II-1) to Formula (II-6), and salts thereof are more preferred as the material compound.

(I-1)
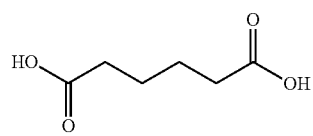

(I-2)
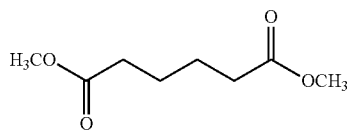

(I-3)
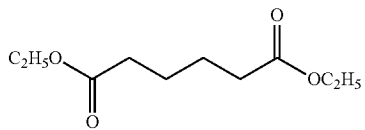

(I-4)
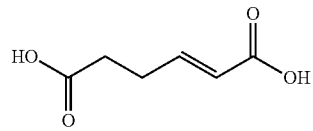

(I-5)
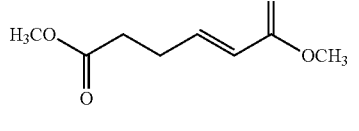

(I-6)
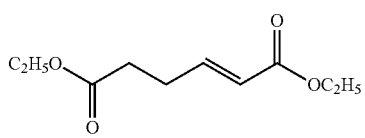

(I-7)
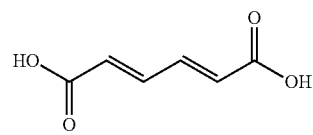

(I-8)
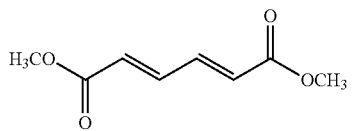

(I-9)
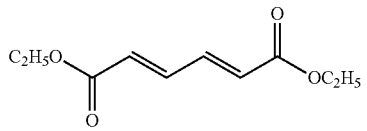

(I-10)
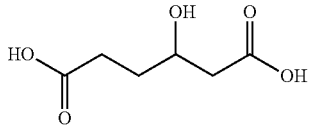

(I-11)
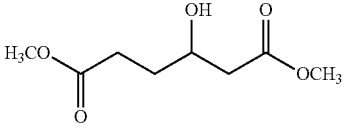

(I-12)
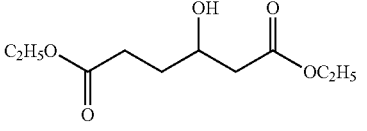

(II-1)
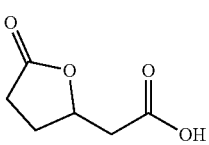

(II-2)
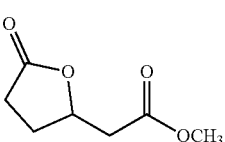

(II-3)
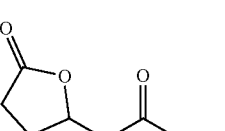

(II-4)
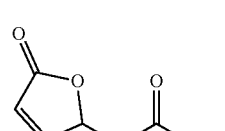

(II-5)
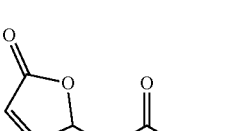

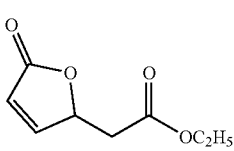

(II-6)

Among the compounds represented by Formula (I-1) to Formula (I-12) and Formula (II-1) to Formula (II-6), and salts thereof, from the viewpoint of ease of the derivation from biomass resources, one or more carboxylic acids selected from the group consisting of adipic acid (I-1), α-hydromuconic acid (I-4), muconic acid (I-7), 3-hydroxyadipic acid (I-10), 3-hydroxyadipic acid-3,6-lactone (II-1), and muconolactone (II-4), and/or a salt(s) thereof may be preferably used as the material compound.

Adipic acid (I-1) can be obtained by derivation from biomass resources. For example, adipic acid can be obtained by fermentative production from plant-derived acetic acid using a microorganism belonging to the genus *Rhodobacter* (WO 2012/137771). Adipic acid can also be obtained by fermentative production from oleic acid derived from vegetable oils using a microorganism belonging to the genus *Candida* (US 2013/157343 A).

α-Hydromuconic acid (I-4) can be obtained by derivation from biomass resources. For example, α-hydromuconic acid (I-4) can be obtained by fermentative production from a carbon source derived from biomass resources, using a naturally occurring or artificially improved microorganism having an ability to produce α-hydromuconic acid. As shown in Scheme 2, α-hydromuconic acid (I-4) can be obtained also by intramolecular dehydration of 3-hydroxyadipic acid (I-10), which is derived from biomass resources (WO 2014/43182). Since one double bond is present in the molecule of α-hydromuconic acid (1-4), α-hydromuconic acid has a cis-isomer and a trans-isomer as geometric isomers. In the production method of the present invention, any of the cis isomer, the trans isomer, and a mixture of the cis isomer and the trans isomer may be used as a material.

Muconic acid (I-7) can be obtained by derivation from biomass resources. For example, muconic acid can be obtained by fermentative production from glucose using a recombinant strain of *Escherichia coli* (US 2013/30125 A). Since two double bonds are present in the molecule of muconic acid (I-7), muconic acid has a cis-cis isomer, a cis-trans isomer, and a trans-trans isomer as geometric isomers. In the production method of the present invention, any of the cis-cis isomer, the cis-trans isomer, the trans-trans isomer, and a mixture of these may be used as a material.

3-Hydroxyadipic acid (I-10) can be obtained by derivation from biomass resources. For example, 3-hydroxyadipic acid (I-10) can be obtained by fermentative production from a carbon source derived from biomass resources, using a naturally occurring or artificially improved microorganism having an ability to produce 3-hydroxyadipic acid. As described in Scheme 2, 3-hydroxyadipic acid (I-10) can be obtained by hydrogen reduction of β-ketoadipic acid which is derived from biomass resources (WO 2014/43182). Since an asymmetric carbon atom is present in the molecule of 3-hydroxyadipic acid (I-10), 3-hydroxyadipic acid has a D-isomer and an L-isomer as optical isomers. In the production method of the present invention, any of the D-isomer, the L-isomer, and a mixture of these may be used as a material.

3-Hydroxyadipic acid-3,6-lactone (II-1) can be obtained by derivation from biomass resources. For example, as shown in Scheme 2, 3-hydroxyadipic acid-3,6-lactone can be synthesized from β-ketoadipic acid which is derived from biomass resources (Metabolism, vol. 38, p. 655-661 (1989)).

β-Ketoadipic acid can be obtained by fermentative production from protocatechuic acid using recombinant *Pseudomonas putida* (JP 2012-59 A). Protocatechuic acid can be obtained by fermentative production from glucose which is a carbon source derived from biomass resources (U.S. Pat. No. 5,272,073 B). Thus, as shown in Scheme 2, β-ketoadipic acid is a compound derived from biomass resources.

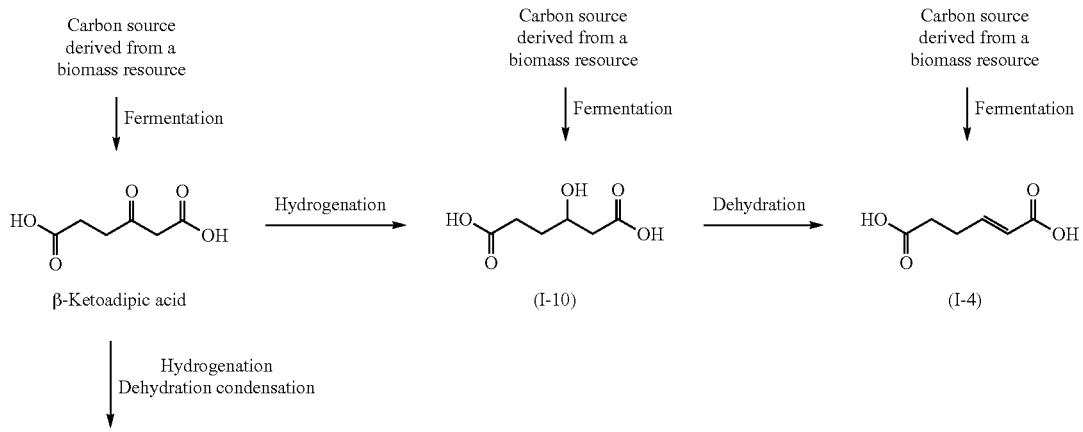

Scheme 2

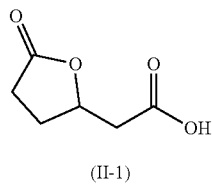

(II-1)

Muconolactone (II-4) can be obtained by derivation from biomass resources. For example, muconolactone can be obtained by fermentative production from protocatechuic acid using recombinant *Pseudomonas putida* (JP 2012-59 A). As described above, protocatechuic acid can be obtained by fermentative production from glucose which is a carbon source derived from biomass resources.

Examples of the salt of the carboxylic acid of the compound include alkali metal salts, alkaline earth metal salts, and ammonium salts. Specific examples of the salt of the carboxylic acid represented by General Formula (I) include monolithium salt, dilithium salt, monosodium salt, disodium salt, monopotassium salt, dipotassium salt, magnesium salt, calcium salt, monoammonium salt, and diammonium salt. Examples of the salt of the carboxylic acid represented by General Formula (II) include lithium salt, sodium salt, potassium salt, magnesium salt, calcium salt, and ammonium salt. A mixture of different salts among these may also be used as the material compound.

Since the fact that adipamide can be formed by amidation of 6-amino-6-oxohexanoic acid in the presence of ammonia is obvious from the facts described in WO 2013/126250 and "Chemical Engineering Research and Design, vol. 88, p. 1067-1072", and from the common technical knowledge of those skilled in the art, 6-amino-6-oxohexanoic acid can be a material compound in the present invention.

WO 2012/141997 describes that adipamide can be formed by hydrogenation of muconic acid amide. Muconic acid amide can therefore be a material compound in the present invention.

"Tetrahedron Letters, vol. 52, p. 6021-6023 (2011)" describes that adipamide can be formed by hydration of adiponitrile using copper or palladium and molecular sieves as catalysts. U.S. Pat. No. 7,285,406 B describes that adipamide can be formed by hydration of adiponitrile using recombinant *E. coli*. Adiponitrile can therefore be a material compound in the present invention.

"Journal of Applied Polymer Science, vol. 124, p. 1707-1715 (2012)" describes that adipamide can be formed by reaction of adipoyl chloride with aqueous ammonia. Adipoyl chloride can therefore be a material compound in the present invention.

Several specific examples of the material compound that can be used for the present invention are shown above. However, the compound is not limited as long as it is a compound from which adipamide can be formed by a chemical and/or biological conversion process of not more than several steps. The material compound may be either a single kind of compound or a mixture of two or more kinds of compounds.

[Catalyst]

The Catalyst Used in the Lactamization Step in the Present Invention is a Catalyst Containing:

a metal oxide mainly containing an oxide(s) of one or more metallic elements selected from the group consisting of metallic elements of group 5 and groups 7 to 14 in the 4th to 6th periods of the periodic table; and a metal and/or a metal compound having a hydrogenation ability.

[Metal Oxide Constituting Catalyst]

The metal oxide constituting the catalyst in the present invention is a metal oxide with which 5-cyanovaleramide can be selectively formed when adipamide is subjected to the same reaction as the lactamization step in the presence of a catalyst composed only of the metal oxide. As shown in the Examples in the present description, the metal oxide is a metal oxide mainly containing an oxide(s) of one or more metallic elements selected from the group consisting of metallic elements of group 5 and groups 7 to 14 in the 4th to 6th periods of the periodic table, and specific examples of the metal oxide include metal oxides mainly containing an oxide(s) of one or more metallic elements selected from the group consisting of vanadium, niobium, tantalum, manganese, technetium, rhenium, iron, ruthenium, osmium, cobalt, rhodium, iridium, nickel, palladium, platinum, copper, silver, gold, zinc, cadmium, mercury, gallium, indium, thorium, germanium, tin, and lead.

In particular, from the viewpoint of availability and the cost, a metal oxide mainly containing an oxide(s) of one or more metallic elements selected from the group consisting of vanadium, niobium, tantalum, manganese, iron, cobalt, nickel, copper, zinc, gallium, indium, thorium, germanium, tin, and lead may be preferably used. A metal oxide mainly containing an oxide(s) of one or more metallic elements selected from the group consisting of niobium, tantalum, manganese, iron, and zinc may be more preferably used. By using a catalyst containing such a metal oxide, and containing a metal and/or a metal compound having a hydrogenation ability, in the lactamization step, formation of by-products that do not contribute to the formation of ε-caprolactam can be suppressed, leading to an improved ε-caprolactam selectivity. This is because, as described later, these metal oxides contribute to the formation of 5-cyanovaleramide from adipamide with high selectivities.

The term "mainly containing" the oxide(s) of the above metallic element(s) herein means a state where the chemical properties of the oxide(s) of the above metallic element(s) are reflected in the chemical surface properties of the metal oxide. For example, in cases where the metal oxide is constituted only with the oxide(s) of the above metallic element(s), it is obvious that the chemical properties of the oxide(s) of the above metallic element(s) are reflected in the chemical surface properties of the metal oxide. Therefore, the metal oxide can be said to be "mainly containing" the oxide(s) of the above metallic element(s). Further, for example, in cases of a composite metal oxide in which the oxide(s) of the above metallic element(s) cover(s) the surface of an oxide of a metallic element (such as silicon) other than the above metallic element(s), when the chemical properties of the oxide(s) of the above metallic element(s) are reflected in the chemical surface properties of the composite metal oxide while the chemical properties of the oxide in the inner side are not reflected in the chemical surface properties of the composite metal oxide, the composite metal oxide can be said to be "mainly containing" the oxide(s) of the above metallic element(s).

Thus, in cases where the surface of an oxide of silicon or the like is covered with the oxide(s) of the above metallic element(s), and where the chemical properties of the oxide(s) of the above metallic element(s) are reflected in the chemical surface properties of the entire metal oxide, the metal oxide can be preferably used in the present invention. In cases where a metal oxide having a large specific surface area such as an oxide of silicon is covered with the oxide(s) of the above metallic element(s), the resulting structure can have an increased surface area of the oxide(s) of the preferred metallic element(s). Therefore, the catalytic activity can be improved, and, when a metal having a hydrogenation ability is to be supported, a preferred support material can be provided.

In cases where the ratio of the oxide(s) of the above metallic element(s) to the composite metal oxide is too small, the metal oxide in the inner side cannot be sufficiently covered, so that the chemical properties of the oxide(s) of the above metallic element(s) tend not to be reflected. On the other hand, in cases where the ratio is too large, the amount of the oxide(s) of the above metallic element(s) to be used increases, and the surface area cannot be increased effectively. Thus, the ratio of the oxide(s) of the above metallic element(s) is preferably 2% by weight to 80% by weight, more preferably 5% by weight to 60% by weight, still more preferably 10% by weight to 40% by weight.

Examples of the method of preparing such a composite metal oxide include the common impregnation method described in "Handbook of Catalysts (Kodansha Ltd.; publ., Dec. 10, 2008), pp. 284-285". The impregnation method is a method in which a support is impregnated with an impregnation liquid containing a component to be supported, and the powder obtained by removal of the impregnation liquid is then dried and calcined to achieve immobilization of the component to be supported on the support. Here, the component to be supported is the oxide(s) of the above metallic element(s), and the support means the metal oxide that supports the oxide(s) of the above metallic element.

The impregnation liquid can be prepared by dissolving a metal salt(s) of the above metallic element(s) in an aqueous solvent and/or an organic solvent. The metal salt used herein may be any of a nitrate, hydrochloric acid salt, acetate, organic salt, and the like.

The temperature at which the support is impregnated is not limited as long as it is not more than 100° C. The impregnation is preferably simply carried out at ambient temperature since no apparatus or operation for cooling or heating is required in this case. The impregnation liquid can be removed by distillation or filtration.

The thus obtained metal oxide support to which the metal salt(s) of the above metallic element(s) is/are attached can be dried by, for example, allowing air to flow therethrough at a temperature of about 80 to 110° C.

The resulting dried metal oxide support to which the metal salt(s) of the above metallic element(s) is/are attached may be calcined at a calcination temperature of 300° C. to 900° C. The atmosphere for the calcination is not limited as long as it contains oxygen. The calcination can be simply carried out under air flow. By the calcination, a composite metal oxide in which the metal oxide(s) of the above metallic element(s) is/are generated on the metal oxide support can be obtained.

Even in cases where a certain metal oxide is a physical mixture of the oxide(s) of the above metallic element(s) and an oxide of a metallic element other than the above metallic element(s), the metal oxide is regarded as "mainly containing" the oxide(s) of the above metallic element(s) in the present invention as long as the chemical properties of the oxide(s) of the above metallic element(s) are mainly reflected in the chemical properties of the metal oxide. For example, even in cases where the metal oxide is a physical mixture of an oxide of iron and an oxide of silicon, the metal oxide is regarded as "mainly containing" the oxide of iron when the chemical properties of the oxide of iron are mainly reflected.

The term "mainly containing" an oxide of a metallic element other than the above metallic element(s) means a state where the chemical properties of the oxide of the metallic element other than the above metallic element(s) are mainly reflected in the chemical properties of the metal oxide.

The term "chemical properties" of the metal oxide means reactivity of the metal oxide observed when adipamide is subjected to the same reaction as the lactamization step in the presence of a catalyst composed only of the metal oxide.

On the other hand, when adipamide is subjected to the same reaction as the lactamization step in the presence of a catalyst which does not contain a metal and/or a metal compound having a hydrogenation ability, and which is composed only of a metal oxide, in cases where the use of the metal oxide leads to a decrease in the selectivity of 5-cyanovaleramide or increases in the selectivities of precursors of by-products that do not contribute to formation of ε-caprolactam, the metal oxide cannot be preferably used in the present invention. Regarding such metal oxides, as shown in Comparative Examples 10 to 17 in the present description, metal oxides mainly containing an oxide(s) of one or more metallic elements selected from the group consisting of metallic elements of group 2, group 3, and group 15, and silicon, more specifically, the metal oxides mainly containing an oxide of aluminum, titanium, or zirconium, or the metal oxides mainly containing an oxide of silicon, used in the methods described in WO 2013/126250, WO 2012/141997, and WO 2016/68108, cannot be preferably used. In cases where a catalyst containing a metal oxide mainly containing an oxide of aluminum, titanium, or zirconium, and containing a metal and/or a metal compound having a hydrogenation ability, is used, formation of by-products that do not contribute to the formation of ε-caprolactam tends to be promoted (see Comparative Examples 1 to 3 in the present description). Since catalysts containing a metal oxide mainly containing an oxide of silicon, and containing a metal having a hydrogenation ability, have insufficient activities, large amounts of intermediates tend to accumulate (see Comparative Example 4 in the present description).

Formation of ε-caprolactam hardly occurs in cases where adipamide is subjected to the same reaction as the lactamization step in the presence of a catalyst which does not contain a metal and/or a metal compound having a hydrogenation ability, and which is composed only of a metal oxide. In such cases, as shown in the following Scheme 3, 5-cyanovaleramide, which is an intermediate formed in the process of formation of ε-caprolactam, is formed from adipamide by unimolecular dehydration of adipamide, but adiponitrile is formed by unimolecular dehydration of 5-cyanovaleramide, and formation of cyclopentanone, cyclopentaneimine, and 1-cyclopenten-1-amine also occurs.

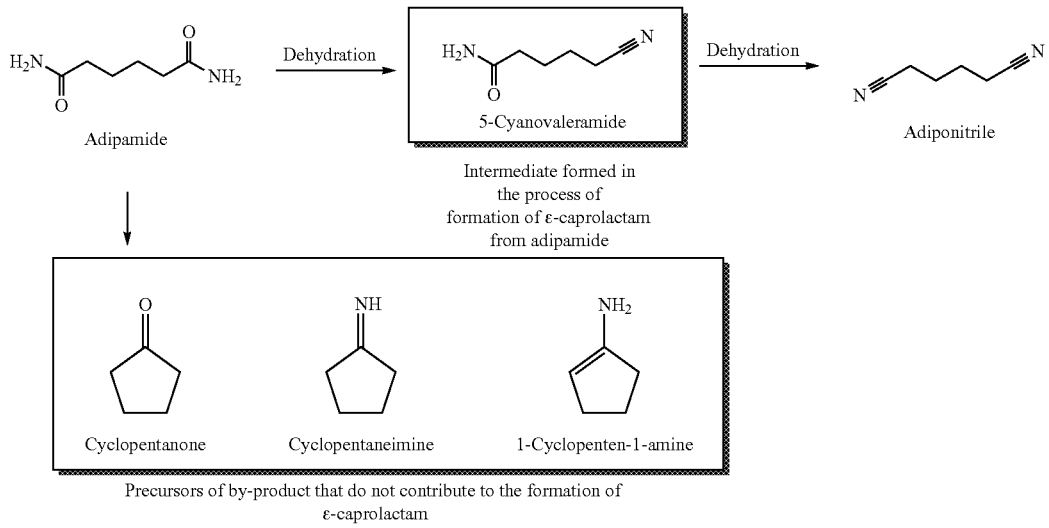

Scheme 3

Precursors of by-product that do not contribute to the formation of ε-caprolactam Reaction of cyclopentanone with hydrogen and ammonia in the presence of a catalyst containing a metal oxide and a metal having a hydrogenation ability causes formation of cyclopentylamine (JP 4750939 B). Hydrogenation of a double bond of cyclopentaneimine or 1-cyclopenten-1-amine causes formation of cyclopentylamine. Thus, cyclopentanone, cyclopentaneimine, and 1-cyclopenten-1-amine can be said to be precursors of by-products that do not contribute to the formation of ε-caprolactam.

Reaction of adiponitrile with hydrogen in the presence of a catalyst containing a metal having a hydrogenation ability causes formation of 6-aminocapronitrile or hexamethylenediamine (U.S. Pat. No. 5,717,090 B). Reaction of 6-aminocapronitrile with water in the presence of a catalyst containing a metal oxide causes formation of 6-aminohexanamide, which is an intermediate formed in the process of formation of ε-caprolactam from adipamide (Green Chemistry, vol. 10, p. 98-103 (2008)). Reaction of hexamethylenediamine with oxygen in the presence of a catalyst having an oxidation ability causes formation of ε-caprolactam (Applied Catalysis A: General, vol. 378, p 33-41 (2010)). However, in cases where the lactamization step in the present invention is carried out under conditions where oxygen is absent, hexamethylenediamine does not contribute to the formation of ε-caprolactam. Thus, adiponitrile does not contribute to the formation of ε-caprolactam in some cases. Therefore, from the viewpoint of the fact that 5-cyanovaleramide better contributes to the formation of ε-caprolactam than adiponitrile does, 5-cyanovaleramide is more preferred as a product from adipamide.

However, since formation of adiponitrile indicates the fact that the reaction is proceeding in the direction in which 5-cyanovaleramide is formed from adipamide, when adipamide is subjected to the same reaction as the lactamization step in the presence of a catalyst composed only of a metal oxide, metal oxides leading to high selectivities of adiponitrile can be preferably used in the present invention compared to metal oxides leading to high selectivities of precursors of by-products that do not contribute to the formation of 6-caprolactam.

[Metal and/or Metal Compound Having Hydrogenation Ability Constituting Catalyst]

The metal/metal compound having a hydrogenation ability constituting the catalyst in the present invention means a metal having an ability to add a hydrogen atom to an unsaturated bond such as a carbon-carbon double bond (C=C), carbon-carbon triple bond (C≡C), carbon-oxygen double bond (C=O), carbon-nitrogen double bond (C=N), or carbon-nitrogen triple bond (C≡N) in the presence of hydrogen; and/or a metal compound thereof. The metal compound having a hydrogenation ability means a compound having a hydrogenation ability containing a metallic element(s), which compound is not constituted only with the metallic element(s). For example, an organic metal complex or an organic metal complex compound containing a central metal and a ligand may be used. An organic metal complex or an organic metal complex compound containing a central metal selected from the following transition metal elements may be especially preferably used.

The metal and/or the metal compound having a hydrogenation ability used in the present invention preferably contain(s) a transition metal element. More specifically, the metal and/or the metal compound preferably contain(s) one or more selected from the group consisting of palladium, platinum, ruthenium, rhodium, rhenium, nickel, cobalt, iron, iridium, osmium, copper, and chromium.

The state of the metal having a hydrogenation ability is not limited as long as it has the hydrogenation ability. The metal may be in any of a cluster state, nanoparticle state, microparticle state, and bulk state.

The clusters, nanoparticles, and microparticles of the metal having a hydrogenation ability may be in a state where they are dispersed in a solution, such as a colloidal state.

The metal and/or the metal compound having a hydrogenation ability alone may be combined with the metal oxide to provide the catalyst to be used in the lactamization step in the present invention. However, from the viewpoint of, for example, saving the amount(s) of the metal(s) used, increasing the active surface of the catalyst, or allowing simple preparation, the metal and/or the metal compound is/are preferably used in a state of being supported on carbon, a metal oxide, a polymer, or the like.

The supporting of the metal having a hydrogenation ability on the carbon or the metal oxide can be carried out by using, in the above-described impregnation method, a metal salt of the metal having a hydrogenation ability instead of the metal salt of the above-described metallic element, and adding, after the calcination, an operation of reducing the metal oxide of the metal having a hydrogenation ability formed on the surface of the carbon or the metal oxide. The reduction of the metal oxide of the metal having a hydrogenation ability formed on the surface of the carbon or the metal oxide can be carried out under hydrogen flow at room temperature to 500° C., or can be carried out by a known reduction method using an alkali metal borohydride such as sodium borohydride or potassium borohydride, or a water-soluble reducing substance such as hydrazine or formaldehyde.

In the above-described impregnation method, supporting of the metal having a hydrogenation ability on the polymer can be carried out by reducing a metal ion attached to the polymer. In cases where calcination is carried out, the calcination is preferably carried out in the absence of oxygen since combustion of the polymer occurs in the presence of oxygen. Reduction of the metal ion having a hydrogenation ability attached to the polymer can be carried out by the above-described reduction method using a water-soluble reducing substance.

The supporting of the metal compound having a hydrogenation ability on the carbon, metal oxide, polymer, or the like can be carried out by adding the support such as the carbon, metal oxide, or polymer to an aqueous solution or an organic solvent solution of the metal compound having a hydrogenation ability or a salt thereof to attach the metal compound on the surface of the support, and then removing the solvent. The removal of the solvent may be carried out under reduced pressure, or may be carried out by calcination in the absence of oxygen.

In cases where the metal and/or metal compound having a hydrogenation ability is/are supported on a support metal oxide, the metal oxide is not limited as long as it is a metal oxide that does not decrease the ε-caprolactam selectivity. The above-described metal oxide mainly containing an oxide(s) of one or more metallic elements selected from the group consisting of metallic elements of group 5 and groups 7 to 14 in the 4th to 6th periods of the periodic table, or silicon dioxide is preferably used.

The amount of the catalyst added may be 0.1 to 200% by weight with respect to the material compound. After completion of the reaction, the catalyst may be recovered and repeatedly used. In cases where the catalyst is used repeatedly, the catalyst is more preferably used after being subjected to an activation treatment by heat treatment under an atmosphere of an inert gas such as nitrogen, helium, or argon, or under hydrogen atmosphere.

[Hydrogen, Ammonia]

Unless otherwise specified, the hydrogen in the present invention means molecular hydrogen.

In the lactamization step, the hydrogen and the ammonia may be independently added to the reactor, or may be added as a mixed gas of the hydrogen and the ammonia. The order of addition of the hydrogen and the ammonia is not limited. The hydrogen and the ammonia may be added at once (batch method), or may be sequentially added (continuous method), to the reactor.

The Hydrogen to be Used May be a Mixed Gas with Nitrogen Gas, Helium Gas, Argon Gas, Water Vapor, and/or the Like.

In cases where the partial pressure of hydrogen is too low, the reaction time is long, while in cases where the partial pressure of hydrogen is too high, it is not preferred from the viewpoint of equipment safety, and moreover, sequential hydrogen reduction of ε-caprolactam may be promoted. Thus, the partial pressure of hydrogen, near ambient temperature, before the beginning of the reaction is preferably 0.1 MPa to 10 MPa (gauge pressure), more preferably 0.3 MPa to 7 MPa (gauge pressure), still more preferably 0.5 MPa to 3 MPa (gauge pressure).

The ammonia to be used may be added to the reactor in either a gaseous state or a liquid state. In cases where the ammonia is added in a liquid state, liquid ammonia or a solution in which ammonia is dissolved may be used. For example, an aqueous ammonia solution, ammonia-dioxane solution, ammonia-chloroform solution, ammonia-ether solution, or ammonia-alcohol solution may be preferably used.

In cases where ammonia in a gas state is used, a mixed gas with nitrogen gas, helium gas, argon gas, water vapor, and/or the like may be used. The partial pressure of the ammonia in the gas state is not limited. However, since, in cases where the partial pressure is too low, the reaction time may be long, the partial pressure before the beginning of the reaction is preferably 0.05 MPa to 5 MPa (gauge pressure) near ambient temperature, more preferably 0.1 MPa to 1 MPa (gauge pressure) at ambient temperature.

Unreacted hydrogen and ammonia remaining after the reaction may be recovered and returned to the reaction system.

Unless otherwise specified, the oxygen in the present invention means molecular oxygen.

The lactamization step is usually preferably carried out in the absence of oxygen. In cases where oxygen is present, the metal and/or the metal compound having a hydrogenation ability contained in the catalyst may be oxidized, leading to a decrease in the hydrogenation activity, and hence to a slow reaction rate in the lactamization step. Moreover, mixing of oxygen with hydrogen may cause explosion. Therefore, also from the viewpoint of equipment safety, the step is preferably carried out under conditions where oxygen is absent.

[Solvent]

The reaction in the lactamization step is preferably carried out in the presence of a solvent. Examples of the solvent to be used include, but are not limited to, alcoholic solvents such as methanol, ethanol, propanol (1-propanol and 2-propanol), butanol (1-butanol, 2-butanol, isobutanol, and tert-butanol), and cyclohexanol; halogen-containing solvents such as carbon tetrachloride, dichloromethane, and chloroform; aliphatic hydrocarbon solvents such as pentane, hexane, heptane, octane, and decane; ether solvents such as dimethyl ether, diethyl ether, methyl-tert-butyl ether, diisopropyl ether, dibutyl ether, 1,2-dimethoxyethane, diglyme, tetrahydrofuran, 1,4-dioxane, and cyclopentyl methyl ether; ester solvents such as methyl acetate, ethyl acetate, n-propyl acetate, and n-butyl acetate; and aqueous solvents. The solvent may be a mixed solvent of two or more of these. Ether solvents such as dimethyl ether, diethyl ether, methyl-tert-butyl ether, diisopropyl ether, dibutyl ether, 1,2-dimethoxyethane, diglyme, tetrahydrofuran, 1,4-dioxane, and cyclopentyl methyl ether; and alcoholic solvents such as methanol, ethanol, propanol (1-propanol and 2-propanol), butanol (1-butanol, 2-butanol, isobutanol, and tert-butanol), and cyclohexanol; may be more preferably used. The solvent is still more preferably 2-propanol, 2-butanol, tert-butanol, cyclohexanol, diisopropyl ether, dibutyl ether, 1,2-dimethoxyethane, diglyme, tetrahydrofuran, or 1,4-dioxane.

[Reaction Temperature]

The reaction temperature in the lactamization step is not limited, and is preferably 100° C. to 350° C., more preferably 150° C. to 300° C., still more preferably 200° C. to 260° C. When the reaction temperature is too low, the reaction tends not to proceed sufficiently, while in cases where the reaction temperature is too high, the ε-caprolactam selectivity tends to be low.

In the present invention, in cases where the reaction method of forming adipamide as an intermediate from the material compound is the same as the reaction method in the lactamization step described in the present description, the reaction for forming ε-caprolactam from the material compound may be carried out continuously in the same reactor (one-pot). The reaction is preferably carried out in the same reactor from the viewpoint of the equipment.

Examples of the material compound with which adipamide can be formed by the same reaction method as in the lactamization step, that is, the material compound with which the one-pot reaction can be carried out, include carboxylic acids represented by General Formula (I) or (II), and salts and esters thereof. Not only from the viewpoint of availability of the material and simplicity of the synthesis, but also from the viewpoint of enabling production of ε-caprolactam by one-pot reaction, a carboxylic acid represented by General Formula (I) or (II), or a salt or an ester thereof, is preferred as the material compound.

In the present invention, in cases where the reaction method of formation of adipamide as an intermediate from the material compound is different from the reaction method of formation of ε-caprolactam from adipamide, the adipamide composition formed from the material compound may be subjected to the lactamization step without carrying out an operation of separation or purification, or may be subjected to isolation and purification of adipamide before the lactamization step.

Examples of methods that may be used for the isolation of adipamide from the adipamide composition include ordinary purification methods such as extraction, adsorption, filtration, precipitation, centrifugation, membrane separation, column chromatography, ion exchange resin treatment, crystallization, and recrystallization.

[Recovery of ε-Caprolactam]

The ε-caprolactam formed by the method of producing ε-caprolactam of the present invention can be recovered by an ordinary separation purification operation(s) such as filtration, extraction, distillation, crystallization, and/or recrystallization after the completion of the reaction.

[Polyamide Polymerization]

The ε-caprolactam obtained by the method of producing ε-caprolactam of the present invention can be used as a material for the production of a polyamide. As a method of producing the polyamide, a known method in which ε-caprolactam is subjected to ring-opening polymerization may be applied (see Osamu Fukumoto eds., "Polyamide Resin Handbook", Nikkan Kogyo Shimbun, Ltd. (January, 1998)).

[Production of 5-Cyanovaleramide]

One mode of the present invention is a method in which 5-cyanovaleramide is formed by conversion of adipamide formed from a material compound, partially utilizing the lactamization step.

As a material compound to be used for the production of 5-cyanovaleramide in one mode of the present invention, a material compound that can be used for the above-described production of ε-caprolactam may be used. That is, as described above, the material compound is not limited as long as it is a compound from which adipamide can be formed by a chemical and/or biological conversion process of not more than several steps, and may be either a compound derived from petroleum or a compound induced from a biomass resource. As described above, the compound is preferably a carboxylic acid represented by General Formula (I) or (II), or a salt or an ester thereof. One or more carboxylic acids selected from the group consisting of adipic acid (I-1), α-hydromuconic acid (I-4), muconic acid (I-7), 3-hydroxyadipic acid (I-10), 3-hydroxyadipic acid-3,6-lactone (II-1), and muconolactone (II-4), and/or a salt(s) thereof may be more preferably used as the material compound.

As a catalyst to be used for the method of production of 5-cyanovaleramide in one mode of the present invention, a metal oxide constituting the catalyst to be used for the above-described lactamization step may be used. That is, a metal oxide mainly containing an oxide(s) of one or more metallic elements selected from the group consisting of metallic elements of group 5 and groups 7 to 14 in the 4th to 6th periods of the periodic table may be used. Specific examples of the metal oxide include metal oxides mainly containing an oxide(s) of one or more metallic elements selected from the group consisting of vanadium, niobium, tantalum, manganese, technetium, rhenium, iron, ruthenium, osmium, cobalt, rhodium, iridium, nickel, palladium, platinum, copper, silver, gold, zinc, cadmium, mercury, gallium, indium, thorium, germanium, tin, and lead. Among these, from the viewpoint of availability and the cost, a metal oxide mainly containing an oxide(s) of one or more metallic elements selected from the group consisting of vanadium, niobium, tantalum, manganese, iron, cobalt, nickel, copper, zinc, gallium, indium, thorium, germanium, tin, and lead may be preferably used. A metal oxide mainly containing an oxide(s) of one or more metallic elements selected from the group consisting of niobium, tantalum, manganese, iron, and zinc may be more preferably used.

In production of 5-cyanovaleramide in one mode of the present invention, the reaction is preferably carried out in the presence of a solvent. A solvent to be used in the above-described lactamization step may be used therefor. Specific examples of the solvent include alcoholic solvents such as methanol, ethanol, propanol (1-propanol and 2-propanol), butanol (1-butanol, 2-butanol, isobutanol, and tert-butanol), and cyclohexanol; halogen-containing solvents such as carbon tetrachloride, dichloromethane, and chloroform; aliphatic hydrocarbon solvents such as pentane, hexane, heptane, octane, and decane; ether solvents such as dimethyl ether, diethyl ether, methyl-tert-butyl ether, diisopropyl ether, dibutyl ether, 1,2-dimethoxyethane, diglyme, tetrahydrofuran, 1,4-dioxane, and cyclopentyl methyl ether; ester solvents such as methyl acetate, ethyl acetate, n-propyl acetate, and n-butyl acetate; and aqueous solvents. The solvent may be a mixed solvent of two or more of these. Ether solvents such as dimethyl ether, diethyl ether, methyl-tert-butyl ether, diisopropyl ether, dibutyl ether, 1,2-dimethoxyethane, diglyme, tetrahydrofuran, 1,4-dioxane, and cyclopentyl methyl ether; and alcoholic solvents such as methanol, ethanol, propanol (1-propanol and 2-propanol), butanol (1-butanol, 2-butanol, isobutanol, and tert-butanol), and cyclohexanol; may be more preferably used. The solvent is still more preferably 2-propanol, 2-butanol, tert-butanol, cyclohexanol, diisopropyl ether, dibutyl ether, 1,2-dimethoxyethane, diglyme, tetrahydrofuran, or 1,4-dioxane.

The reaction temperature for carrying out the production of 5-cyanovaleramide in one mode of the present invention is not limited, and is preferably 100° C. to 350° C., more preferably 150° C. to 300° C., still more preferably 200° C. to 260° C.

The 5-cyanovaleramide formed can be used as an intermediate for ε-caprolactam.

EXAMPLES

The present invention is described below in more detail by way of Examples. However, the present invention is not limited to the Examples below. In the Reference Examples, Examples, and Comparative Examples, the reaction results are defined according to the following equations.

Material compound conversion (%)=((Fed material compound (mol)−unreacted material compound (mol))/Fed material compound (mol))×100.

Selectivity of product (%)=amount of product formed (mol)/(Fed material compound (mol)−unreacted material compound (mol))×100.

Intermediate selectivity (%)=selectivity of 6-amino-6-oxohexanoic acid (%)+selectivity of adipamide (%).

ε-Caprolactam selectivity (%)=selectivity of 5-cyanovaleramide (%)+selectivity of 6-aminohexanamide (%)+selectivity of ε-caprolactam (%)+selectivity of hexamethyleneimine (%).

By-product selectivity (%)=selectivity of cyclopentylamine (%)+selectivity of cyclopentanecarboxamide (%).

By-product precursor selectivity (%)=selectivity of cyclopentanone (%)+selectivity of 1-cyclopenten-1-amine (%)+selectivity of cyclopentaneimine (%).

Reaction solutions, and aqueous solutions of reaction solution concentrates were analyzed by gas chromatography (GC) and high-performance liquid chromatography (HPLC), respectively. The product was quantified with an absolute calibration curve prepared using standard samples. Quantitative analysis of 5-cyanovaleramide, ε-caprolactam, hexamethyleneimine, cyclopentylamine, cyclopentanecarboxamide, adiponitrile, cyclopentanone, 1-cyclopenten-1-amine, and cyclopentaneimine was carried out mainly by GC, and quantitative analysis of adipic acid, muconic acid, α-hydromuconic acid, 3-hydroxyadipic acid, 3-hydroxyadipic acid-3,6-lactone, muconolactone, 6-amino-6-oxohexanoic acid, adipamide, and 6-aminohexanamide was carried out mainly by HPLC. The analysis conditions of GC and HPLC were as follows.

[GC Analysis Conditions]
GC apparatus: GC2010 plus (manufactured by Shimadzu Corporation)
Column: InertCap for amines; length, 30 m; inner diameter, 0.32 mm (manufactured by GL Sciences Inc.)
Carrier gas: helium; constant linear velocity (40.0 cm/second)
Vaporizing chamber temperature: 250° C.
Detector temperature: 250° C.
Column oven temperature: 100° C.→(10° C./minute)→230° C. for 3 minutes (16 minutes in total)
Detector: FID.
[HPLC Analysis Conditions]
HPLC apparatus: Prominence (manufactured by Shimadzu Corporation)
Column: Synergi hydro-RP (manufactured by Phenomenex Inc.); length, 250 mm; inner diameter, 4.60 mm; particle size, 4 μm
Mobile phase: 0.1% by weight aqueous phosphoric acid solution/acetonitrile=95/5 (volume ratio)
Flow rate: 1.0 mL/minute
Detector: UV (210 nm)
Column temperature: 40° C.

(Reference Example 1) Providing of α-Hydromuconic Acid (I-4)

The α-hydromuconic acid used in the present invention was provided by chemical synthesis. First, 1.5 of superdehydrated tetrahydrofuran (manufactured by Wako Pure Chemical Industries, Ltd.) was added to 13.2 g (0.1 mol) of succinic acid monomethyl ester (manufactured by Wako Pure Chemical Industries, Ltd.), and 16.2 g (0.1 mol) of carbonyldiimidazole (manufactured by Wako Pure Chemical Industries, Ltd.) was added thereto with stirring, followed by stirring the resulting mixture under nitrogen atmosphere at room temperature for 1 hour. To this suspension, 15.6 g (0.1 mol) of malonic acid monomethyl ester potassium salt (manufactured by Tokyo Chemical Industry Co., Ltd.) and 9.5 g (0.1 mol) of magnesium chloride (manufactured by Nacalai Tesque, Inc.) were added. The resulting mixture was stirred under nitrogen atmosphere at room temperature for 1 hour, and then stirred at 40° C. for 12 hours. After completion of the reaction, 0.05 of 1 mol/L hydrochloric acid was added to the mixture, and extraction with ethyl acetate was carried out. By separation purification by silica gel column chromatography (hexane:ethyl acetate=1:5), 13.1 g of pure 3-oxohexanedicarboxylic acid dimethyl ester was obtained. Yield: 70%.

To 10 g (0.05 mol) of the 3-oxohexanedicarboxylic acid dimethyl ester obtained, 0.1 of methanol (manufactured by Kokusan Chemical Co., Ltd.) was added, and 2.0 g (0.05 mol) of sodium borohydride (manufactured by Wako Pure Chemical Industries, Ltd.) was added to the resulting mixture with stirring, followed by stirring the mixture at room temperature for 1 hour. Subsequently, 0.02 of 5 mol/L aqueous sodium hydroxide solution was added thereto, and the resulting mixture was stirred at room temperature for 2 hours. After completion of the reaction, the pH was adjusted to 1 with 5 mol/L hydrochloric acid, and the mixture was then concentrated using a rotary evaporator. By recrystallization with water, 7.2 g of pure α-hydromuconic acid was obtained. Yield: 95%.

$^1$H-NMR (400 MHz, CD$_3$OD): δ2.48 (m, 4H), δ5.84 (d, 1H), δ6.96 (m, 1H).

(Reference Example 2) Providing of 3-Hydroxyadipic Acid (I-10)

The 3-hydroxyadipic acid used in the present invention was provided by chemical synthesis. First, 1.5 of superdehydrated tetrahydrofuran (manufactured by Wako Pure Chemical Industries, Ltd.) was added to 13.2 g (0.1 mol) of succinic acid monomethyl ester (manufactured by Wako Pure Chemical Industries, Ltd.), and 16.2 g (0.1 mol) of carbonyldiimidazole (manufactured by Wako Pure Chemical Industries, Ltd.) was added thereto with stirring, followed by stirring the resulting mixture under nitrogen atmosphere at room temperature for 1 hour. To this suspension, 15.6 g (0.1 mol) of malonic acid monomethyl ester potassium salt (manufactured by Tokyo Chemical Industry Co., Ltd.) and 9.5 g (0.1 mol) of magnesium chloride (manufactured by Nacalai Tesque, Inc.) were added. The resulting mixture was stirred under nitrogen atmosphere at room temperature for 1 hour, and then stirred at 40° C. for 12 hours. After completion of the reaction, 0.05 of 1 mol/L hydrochloric acid was added to the mixture, and extraction with ethyl acetate was carried out. By separation purification by silica gel column chromatography (hexane:ethyl acetate=1:5), 13.1 g of pure 3-oxohexanedicarboxylic acid dimethyl ester was obtained. Yield: 70%.

To 10 g (0.05 mol) of the 3-oxohexanedicarboxylic acid dimethyl ester obtained, 0.1 of methanol (manufactured by Kokusan Chemical Co., Ltd.) was added, and 0.02 of 5 mol/L aqueous sodium hydroxide solution was added to the resulting mixture with stirring, followed by stirring the mixture at room temperature for 2 hours. After completion of the reaction, the pH was adjusted to 1 with 5 mol/L hydrochloric acid. Subsequently, 2.0 g (0.05 mol) of sodium borohydride (manufactured by Wako Pure Chemical Industries, Ltd.) was added thereto, and the resulting mixture was stirred at room temperature for 2 hours. After completion of the reaction, the mixture was concentrated using a rotary evaporator. By recrystallization with water, 7.2 g of pure 3-hydroxyadipic acid was obtained. Yield: 95%.

$^1$H-NMR (400 MHz, $CD_3OD$): δ1.70 (m, 1H), δ1.83 (m, 1H), δ2.42 (m, 4H), δ4.01 (m, 1H).

(Reference Example 3) Providing of
3-Hydroxyadipic Acid-3,6-Lactone (II-1)

The 3-hydroxyadipic acid-3,6-lactone used in the present invention was provided by chemical synthesis. First, 1.5 of super-dehydrated tetrahydrofuran (manufactured by Wako Pure Chemical Industries, Ltd.) was added to 13.2 g (0.1 mol) of succinic acid monomethyl ester (manufactured by Wako Pure Chemical Industries, Ltd.), and 16.2 g (0.1 mol) of carbonyldiimidazole (manufactured by Wako Pure Chemical Industries, Ltd.) was added thereto with stirring, followed by stirring the resulting mixture under nitrogen atmosphere at room temperature for 1 hour. To this suspension, 15.6 g (0.1 mol) of malonic acid monomethyl ester potassium salt (manufactured by Tokyo Chemical Industry Co., Ltd.) and 9.5 g (0.1 mol) of magnesium chloride (manufactured by Nacalai Tesque, Inc.) were added. The resulting mixture was stirred under nitrogen atmosphere at room temperature for 1 hour, and then stirred at 40° C. for 12 hours. After completion of the reaction, 0.05 L of 1 mol/L hydrochloric acid was added to the mixture, and extraction with ethyl acetate was carried out. By separation purification by silica gel column chromatography (hexane:ethyl acetate=1:5), 13.1 g of pure 3-oxohexanedicarboxylic acid dimethyl ester was obtained. Yield: 70%.

To 10 g (0.05 mol) of the 3-oxohexanedicarboxylic acid dimethyl ester obtained, 0.1 of methanol (manufactured by Kokusan Chemical Co., Ltd.) was added, and 0.02 of 5 mol/L aqueous sodium hydroxide solution was added to the resulting mixture with stirring, followed by stirring the mixture at room temperature for 2 hours. After completion of the reaction, the pH was adjusted to 1 with 5 mol/L hydrochloric acid. Subsequently, 2.0 g (0.05 mol) of sodium borohydride (manufactured by Wako Pure Chemical Industries, Ltd.) was added thereto, and the resulting mixture was stirred at room temperature for 2 hours. After completion of the reaction, the mixture was concentrated using a rotary evaporator. By recrystallization with water, 7.2 g of pure 3-hydroxyadipic acid was obtained. Yield: 95%.

$^1$H-NMR (400 MHz, $CD_3OD$): δ1.70 (m, 1H), δ1.83 (m, 1H), δ2.42 (m, 4H), δ4.01 (m, 1H).

To 7.2 g (0.044 mol) of the pure 3-hydroxyadipic acid obtained, 0.1 of ultrapure water was added, and 0.01 of 1 mol/L sulfuric acid was added thereto with stirring, followed by stirring the resulting mixture at 100° C. for 2 hours. After completion of the reaction, the mixture was concentrated using a rotary evaporator. By separation purification by silica gel column chromatography (chloroform:methanol=10:1), 5.8 g of pure 3-hydroxyadipic acid-3,6-lactone was obtained. Yield: 90%.

$^1$H-NMR (400 MHz, $D_2O$): δ2.03 (m, 1H), δ2.04-2.90 (m, 5H), δ5.00 (m, 1H).

(Reference Example 4) Providing of Catalyst

To an aqueous solution prepared by dissolving 0.13 g of palladium nitrate ($Pd(NO_3)_2 \cdot 2H_2O$, manufactured by Alfa Aesar) in 10 mL of water, 1 g of niobium oxide ($Nb_2O_5$, manufactured by Wako Pure Chemical Industries, Ltd.) was added, and the resulting mixture was stirred at room temperature for 3 hours. Water was evaporated using an evaporator at 20 mmHg at 40° C., and the resulting powder was dried at 110° C. overnight, followed by calcination under air flow at 500° C. for 4 hours. Subsequently, the powder was treated under hydrogen flow at 400° C. for 2 hours to thereby obtain 5% palladium-supporting niobium oxide (5% $Pd/Nb_2O_5$). Here, "5%" means that the ratio of palladium to the total weight of palladium and the metal oxide is 5% by weight at the time of feeding the materials. In addition, a different amount of palladium nitrate was used to obtain 1.7% palladium-supporting niobium oxide (1.7% $Pd/Nb_2O_5$).

Similarly, tantalum oxide ($Ta_2O_5$, manufactured by Wako Pure Chemical Industries, Ltd.), zirconium oxide ($ZrO_2$, reference catalyst JRC—ZRO-3 according to Catalysis Society of Japan), titanium oxide (anatase type) ($TiO_2$, reference catalyst JRC-TIO-1 according to Catalysis Society of Japan), silicon dioxide ($SiO_2$, CARiACT G6, manufactured by Fuji Silysia Chemical Ltd.), and α-iron oxide (α-$Fe_2O_3$, manufactured by Wako Pure Chemical Industries, Ltd.) were used instead of niobium oxide to prepare 5% palladium-supporting tantalum oxide (5% $Pd/Ta_2O_5$), 5% palladium-supporting zirconium oxide (5% $Pd/ZrO_2$), 5% palladium-supporting titanium oxide (5% $Pd/TiO_2$), 5% palladium-supporting silicon dioxide (5% $Pd/SiO_2$), and 5% palladium-supporting α-iron oxide (5% $Pd/\alpha\text{-}Fe_2O_3$), respectively. Similarly, nickel nitrate hexahydrate (Ni$(NO_3)_2 \cdot 6H_2O$, manufactured by Wako Pure Chemical Industries, Ltd.) was used instead of palladium nitrate to prepare 5% nickel-supporting niobium oxide (5% $Ni/Nb_2O_5$), 10% nickel-supporting silicon dioxide (10% $Ni/SiO_2$), and 20% nickel-supporting silicon dioxide (20% $Ni/SiO_2$).

Similarly, nickel nitrate hexahydrate and cobalt nitrate hexahydrate ($Co(NO_3)_2 \cdot 6H_2O$, manufactured by Wako Pure Chemical Industries, Ltd.), or nickel nitrate hexahydrate and iron nitrate nonahydrate ($Fe(NO_3)_3 \cdot 9H_2O$, manufactured by Wako Pure Chemical Industries, Ltd.), were used to prepare 10% nickel-10% cobalt-supporting silicon dioxide (10% Ni-10% $Co/SiO_2$) or 10% nickel-10% iron-supporting silicon dioxide (10% Ni-10% $Fe/SiO_2$), respectively.

(Reference Example 5) Preparation of Indium
Oxide-Supporting Silicon Dioxide

To an aqueous solution prepared by dissolving 2.62 g of indium nitrate trihydrate ($In(NO_3)_3 \cdot 3H_2O$, manufactured by Wako Pure Chemical Industries, Ltd.) in 40 mL of water, 4.1 g of silicon dioxide ($SiO_2$, CARiACT G6, manufactured by Fuji Silysia Chemical Ltd.) was added, and the resulting mixture was stirred at room temperature for 15 hours. Water was evaporated using an evaporator at 20 mmHg at 40° C., and the resulting powder was dried at 110° C. overnight, followed by calcination under air flow at 600° C. for 4 hours, to obtain 20% indium oxide-supporting silicon dioxide (20% $In_2O_3/SiO_2$). Here, "20%" means that the ratio of indium oxide to the total weight of indium oxide-supporting silicon dioxide is 20% by weight.

(Reference Example 6) Production of ε-Caprolactam Using Adipamide as Material

To a stainless steel autoclave having a capacity of 0.1 (manufactured by Taiatsu Techno Corporation), 0.144 g of adipamide (Tokyo Chemical Industry Co., Ltd.), 50 mL of dioxane (Wako Pure Chemical Industries, Ltd.), and 0.025 g of Palladium, 5% on gamma alumina powder, reduced (5% $Pd/Al_2O_3$, manufactured by Alfa aesar) were added. With stirring at 500 rpm at room temperature, the inside of the autoclave was purged with nitrogen, and ammonia gas was introduced thereto such that the partial pressure of ammonia gas in the autoclave was adjusted to 0.18 MPa (gauge pressure), followed by keeping the pressure for 45 minutes. Thereafter, while the stirring was continued, hydrogen was introduced thereto such that the partial pressure of hydrogen in the autoclave was adjusted to 0.72 MPa (gauge pressure) (total pressure (gauge pressure): 0.90 MPa). Subsequently, the temperature in the autoclave was increased to 250° C. After keeping the temperature at 250° C. for 3 hours, the autoclave was allowed to cool to room temperature, and the gas in the autoclave was released to allow the pressure to decrease to ambient pressure, followed by recovering the reaction solution. After addition of 50 mL of water, the reaction solution was mixed, and the catalyst was removed by centrifugation. The supernatant was then analyzed by GC and HPLC. The results are shown in Table 1.

(Reference Example 7) Production of ε-Caprolactam Using Adipamide as Material

To a stainless steel autoclave having a capacity of 0.2 (manufactured by Taiatsu Techno Corporation), 0.3 g of adipamide (Tokyo Chemical Industry Co., Ltd.), 100 mL of dioxane (Kanto Chemical Co., Inc.), and 0.05 g of Palladium, 5% on gamma alumina powder, reduced (5% $Pd/Al_2O_3$, manufactured by Alfa Aesar) were added. With stirring at 1000 rpm at room temperature, the inside of the autoclave was purged with nitrogen, and ammonia gas was introduced thereto such that the partial pressure of ammonia gas in the autoclave was adjusted to 0.35 MPa (gauge pressure), followed by keeping the pressure for 45 minutes. While the stirring was continued, hydrogen was introduced thereto such that the partial pressure of hydrogen in the autoclave was adjusted to 1.35 MPa (gauge pressure) (total pressure (gauge pressure): 1.70 MPa). Subsequently, the temperature in the autoclave was increased to 250° C. for 1 hour. After keeping the temperature at 250° C. for 3 hours, the autoclave was allowed to cool to room temperature, and the gas in the autoclave was released to allow the pressure to decrease to ambient pressure, followed by recovering the reaction solution. After addition of 100 mL of water, the reaction solution was mixed, and the catalyst was removed by centrifugation. The supernatant was then analyzed by GC and HPLC. The results are shown in Table 1.

(Reference Example 8) Production of ε-Caprolactam Using Adipamide as Material

A reaction was carried out in the same manner as in Reference Example 6 except that a mixture of 0.1 g of 10% nickel-supporting silicon dioxide and 0.05 g of α-iron oxide (10% $Ni/SiO_2$+α-$Fe_2O_3$) was added instead of 5% $Pd/Al_2O_3$, and that the temperature in the autoclave was increased to 230° C. and then kept at 230° C. for 3 hours. After the autoclave was allowed to cool to room temperature, the gas in the autoclave was released to allow the pressure to decrease to ambient pressure, followed by recovering the reaction solution. The catalyst was removed by filtration, and the supernatant was analyzed by GC. The supernatant was concentrated with a rotary evaporator (Tokyo Rikakikai Co., Ltd.). An aqueous solution of the resulting concentrate was prepared, and analyzed by HPLC. The results are shown in Table 1.

TABLE 1

Production of ε-caprolactam using adipamide as a material

| | Material | Catalyst | Adipamide conversion (%) | By-product selectivity (%) | ε-Caprolactam selectivity (%) |
|---|---|---|---|---|---|
| Reference Example 6 | Adipamide | 5% $Pd/Al_2O_3$ | 76.9 | 36.7 | 46.6 |
| Reference Example 7 | Adipamide | 5% $Pd/Al_2O_3$ | 98.3 | 25.8 | 53.9 |
| Reference Example 8 | Adipamide | 10% $Ni/SiO_2$ + α-$Fe_2O_3$ | 78.8 | 0.5 | 94.7 |

As shown in Reference Examples 6 and 7 in Table 1, in cases where adipamide was used as the material, and palladium-supporting aluminum oxide was used as the catalyst, remarkable formation of by-products that do not contribute to formation of ε-caprolactam occurred, resulting in insufficient ε-caprolactam selectivities. On the other hand, as shown in Reference Example 8, in the case where the catalyst to be used in the present invention was used, by-products that do not contribute to formation of ε-caprolactam decreased, resulting in a high ε-caprolactam selectivity.

(Reference Example 9) Providing of α-Hydromuconic Acid Dimethyl Ester (I-5)

To 5.0 g (0.035 mol) of the α-hydromuconic acid obtained in Reference Example 1, 50 mL of methanol (manufactured by Kokusan Chemical Co., Ltd.) was added to dissolve the α-hydromuconic acid completely. A solution of diazomethane in diethyl ether (containing 0.07 mol of diazomethane) was added thereto with stirring, and the resulting mixture was stirred at room temperature for 3 hours. After completion of the reaction, methanol was removed by distillation using a rotary evaporator, and separation purification by silica gel chromatography (hexane:ethyl acetate=9:1) was carried out to obtain 5.4 g of pure α-hydromuconic acid dimethyl ester. Yield: 90%.

$^1$H-NMR (400 MHz, $CDCl_3$): δ2.46-2.57 (m, 4H), δ3.69 (s, 3H), δ3.72 (s, 3H) δ5.86 (m, 1H), δ6.91-7.02 (m, 1H).

(Example 1) Production of ε-Caprolactam Using Adipic Acid (I-1) as Material Compound To a stainless steel autoclave having a capacity of 0.1 (manufactured by Taiatsu Techno Corporation), 0.146 g of adipic acid (manufactured by Wako Pure Chemical Industries, Ltd.), 50 mL of dioxane (manufactured by Wako Pure Chemical Industries, Ltd.), and 0.1 g of 5% palladium-supporting niobium oxide (5% Pd/Nb$_2$O$_5$) prepared in Reference Example 4 were added. The temperature in the autoclave was adjusted to 30° C., and, with stirring at a stirring rate of 500 rpm, the inside of the autoclave was purged with nitrogen, and ammonia gas was introduced thereto such that the partial pressure of ammonia gas in the autoclave was adjusted to 0.18 MPa (gauge pressure), followed by keeping the pressure for 45 minutes. Thereafter, while the stirring was continued, hydrogen was introduced thereto such that the partial pressure of hydrogen in the autoclave was adjusted to 0.72 MPa (gauge pressure) (total pressure (gauge pressure): 0.90 MPa). Subsequently, the temperature in the autoclave was increased to 250° C. After keeping the temperature at 250° C. for 3 hours, the autoclave was allowed to cool to room temperature, and the gas in the autoclave was released to allow the pressure to decrease to ambient pressure, followed by recovering the reaction solution. The catalyst was removed by filtration, and the supernatant was analyzed by GC. The supernatant was concentrated with a rotary evaporator (manufactured by Tokyo Rikakikai Co., Ltd.). An aqueous solution of the resulting concentrate was prepared, and analyzed by HPLC. The results are shown in Table 2.

(Example 2) Production of ε-Caprolactam Using Adipic Acid (I-1) as Material Compound A reaction was carried out in the same manner as in Example 1 except that 5% nickel-supporting niobium oxide (5% Ni/Nb$_2$O$_5$) prepared in Reference Example 4 was used as the catalyst. The results are shown in Table 2.

(Example 3) Production of ε-Caprolactam Using Adipic Acid (I-1) as Material Compound A reaction was carried out in the same manner as in Example 1 except that 5% palladium-supporting tantalum oxide (5% Pd/Ta$_2$O$_5$) prepared in Reference Example 4 was used as the catalyst. The results are shown in Table 2.

(Comparative Example 1) Production of ε-Caprolactam Using Adipic Acid (I-1) as Material Compound A reaction was carried out in the same manner as in Example 1 except that Palladium, 5% on gamma alumina powder, reduced (5% Pd/Al$_2$O$_3$, manufactured by Alfa Aesar) was used as the catalyst. The results are shown in Table 2.

(Comparative Example 2) Production of ε-Caprolactam Using Adipic Acid (I-1) as Material Compound A reaction was carried out in the same manner as in Example 1 except that 5% palladium-supporting zirconium oxide (5% Pd/ZrO$_2$) prepared in Reference Example 4 was used as the catalyst. The results are shown in Table 2.

(Comparative Example 3) Production of ε-Caprolactam Using Adipic Acid (I-1) as Material Compound A reaction was carried out in the same manner as in Example 1 except that 5% palladium-supporting titanium oxide (5% Pd/TiO$_2$) prepared in Reference Example 4 was used as the catalyst. The results are shown in Table 2.

(Comparative Example 4) Production of ε-Caprolactam Using Adipic Acid (I-1) as Material Compound A reaction was carried out in the same manner as in Example 1 except that 5% palladium-supporting silicon dioxide (5% Pd/SiO$_2$) prepared in Reference Example 4 was used as the catalyst. The results are shown in Table 2.

(Example 4) Production of ε-Caprolactam Using Muconic Acid (1-7) as Material Compound A reaction was carried out in the same manner as in Example 1 except that 0.142 g of trans, trans (t,t)-muconic acid (manufactured by Sigma-Aldrich) was used instead of adipic acid, that the stirring rate was set to 800 rpm, and that the temperature in the autoclave was increased to 180° C. and then kept for 1 hour, followed by increasing the temperature to 250° C. and keeping the temperature at 250° C. for 5 hours. The results are shown in Table 2.

(Comparative Example 5) Production of ε-Caprolactam Using Muconic Acid (1-7) as Material Compound A reaction was carried out in the same manner as in Example 4 except that Palladium, 5% on gamma alumina powder, reduced (5% Pd/Al$_2$O$_3$, manufactured by Alfa aesar) was used as the catalyst. The results are shown in Table 2.

(Example 5) Production of ε-Caprolactam Using Adipic Acid (I-1) as Material Compound A reaction was carried out in the same manner as in Example 1 except that 5% palladium-supporting α-iron oxide (5% Pd/α-Fe$_2$O$_3$) prepared in Reference Example 4 was used as the catalyst. The results are shown in Table 2.

(Example 6) Production of ε-Caprolactam Using Adipic Acid (I-1) as Material Compound A reaction was carried out in the same manner as in Example 1 except that a physical mixture of 0.1 g of 10% nickel-supporting silicon dioxide prepared in Reference Example 4 and 0.05 g of α-iron oxide (manufactured by Wako Pure Chemical Industries, Ltd.) (10% Ni/SiO$_2$+α-Fe$_2$O$_3$) was used as the catalyst. The results are shown in Table 2.

(Example 7) Production of ε-Caprolactam Using α-Hydromuconic Acid (I-4) as Material Compound A reaction was carried out in the same manner as in Example 4 except that 0.144 g of α-hydromuconic acid provided in Reference Example 1 was used, and that a temperature of 250° C. was kept for 3 hours. The results are shown in Table 2.

(Comparative Example 6) Production of ε-Caprolactam Using α-Hydromuconic Acid (I-4) as Material Compound A reaction was carried out in the same manner as in Example 7 except that Palladium, 5% on gamma alumina powder, reduced (5% Pd/Al$_2$O$_3$, manufactured by Alfa aesar) was used as the catalyst. The results are shown in Table 2.

(Example 8) Production of ε-Caprolactam Using 3-Hydroxyadipic Acid (I–10) as Material Compound A reaction was carried out in the same manner as in Example 4 except that 0.160 g of 3-hydroxyadipic acid provided in Reference Example 2 was used instead of muconic acid, and that 0.3 g of 1.7% palladium-supporting niobium oxide (1.7% Pd/Nb$_2$O$_5$) prepared in Reference Example 4 was used as the catalyst. The results are shown in Table 2.

(Comparative Example 7) Production of ε-Caprolactam Using 3-Hydroxyadipic Acid (I–10) as Material Compound A reaction was carried out in the same manner as in Example except that Palladium, 5% on gamma alumina powder, reduced (5% Pd/Al$_2$O$_3$, manufactured by Alfa aesar) was used as the catalyst. The results are shown in Table 2.

(Example 9) Production of ε-Caprolactam Using 3-Hydroxyadipic Acid-3,6-Lactone (II-1) as Material Compound To a stainless steel autoclave having a capacity of 0.1 (manufactured by Taiatsu Techno Corporation), 0.144 g of 3-hydroxyadipic acid-3,6-lactone provided in Reference Example 3, 50 mL of dioxane (Wako Pure Chemical Industries, Ltd.), and Palladium, 5% on gamma alumina powder, reduced (5% Pd/Al$_2$O$_3$, manufactured by Alfa aesar) were added. The temperature in the autoclave was adjusted to 30° C., and, with stirring at a stirring rate of 500 rpm, the inside of the autoclave was purged with nitrogen, and hydrogen was introduced thereto such that the partial pressure of hydrogen in the autoclave was adjusted to 0.90 MPa (gauge pressure). Subsequently, the temperature in the autoclave was increased to 230° C., and then the temperature was kept at 230° C. for 12 hours, followed by allowing the autoclave to cool to room temperature. The gas in the autoclave was released to allow the pressure to decrease to ambient pressure, and the reaction solution was recovered. Filtration was carried out to separate 5% Pd/Al$_2$O$_3$, and the supernatant was returned into the autoclave. After addition of 0.1 g of 5% palladium-supporting niobium oxide (5% Pd/Nb$_2$O$_5$) thereto, the temperature in the autoclave was adjusted to 30° C. With stirring at a stirring rate of 500 rpm, the inside of the autoclave was purged with nitrogen, and ammonia gas was introduced thereto such that the partial pressure of ammonia gas in the autoclave was adjusted to 0.18 MPa (gauge pressure), followed by keeping the pressure for 45 minutes. Thereafter, while the stirring was continued, hydrogen was introduced thereto such that the partial pressure of hydrogen in the autoclave was adjusted to 0.72 MPa (gauge pressure) (total pressure (gauge pressure): 0.90 MPa). Subsequently, the temperature in the autoclave was increased to 250° C. After keeping the temperature at 250° C. for 5 hours, the autoclave was allowed to cool to room temperature, and the gas in the autoclave was released to allow the pressure to decrease to ambient pressure, followed by recovering the reaction solution. The catalyst was removed by filtration, and the supernatant was analyzed by GC. The supernatant was concentrated with a rotary evaporator (Tokyo Rikakikai Co., Ltd.). An aqueous solution of the resulting concentrate was prepared, and analyzed by HPLC. The material conversion was 100%; the intermediate selectivity was 3.3%; the by-product selectivity was 2.8%; and the ε-caprolactam selectivity was 84.1%.

(Comparative Example 8) Production of ε-Caprolactam Using 3-Hydroxyadipic Acid-3,6-Lactone (II-1) as Material Compound Throughout the process, the reaction was carried out in the same manner as in Example 9 except that Palladium, 5% on gamma alumina powder, reduced (5% Pd/Al$_2$O$_3$, manufactured by Alfa aesar) was used as the catalyst. The material conversion was 100%; the intermediate selectivity was 6.7%; the by-product selectivity was 21.2%; and the ε-caprolactam selectivity was 60.5%.

(Example 10) Production of ε-Caprolactam Using Adipic Acid (I–1) as Material Compound A reaction was carried out in the same manner as in Example 1 except that a physical mixture of 0.05 g of 10% nickel-10% cobalt-supporting silicon dioxide prepared in Reference Example 4 and 0.05 g of α-iron oxide (manufactured by Wako Pure Chemical Industries, Ltd.) (10% Ni-10% Co/SiO$_2$+α-Fe$_2$O$_3$) was used as the catalyst. The results are shown in Table 2.

(Example 11) Production of ε-Caprolactam Using Adipic Acid (I-1) as Material Compound A reaction was carried out in the same manner as in Example 10 except that 10% nickel-10% iron-supporting silicon dioxide (10% Ni-10% Fe/SiO$_2$) was used instead of 10% nickel-10% cobalt-supporting silicon dioxide. The results are shown in Table 2.

(Example 12) Production of ε-Caprolactam Using α-Hydromuconic Acid (I-4) as Material Compound A reaction was carried out in the same manner as in Example 7 except that a physical mixture of 0.1 g of 10% nickel-supporting silicon dioxide and 0.1 g of α-iron oxide (manufactured by Wako Pure Chemical Industries, Ltd.) (10% Ni/SiO$_2$+α-Fe$_2$O$_3$) was used as the catalyst. The results are shown in Table 2.

(Example 13) Production of ε-Caprolactam Using Diammonium Adipate as Material Compound A reaction was carried out in the same manner as in Example 1 except that 0.18 g of diammonium adipate (manufactured by Wako Pure Chemical Industries, Ltd.) was used as the material compound, that 50 mL of tert-butanol (manufactured by Wako Pure Chemical Industries, Ltd.) was used as the solvent, that a physical mixture of 0.1 g of 20% nickel-supporting silicon dioxide, 0.05 g of α-iron oxide (manufactured by Wako Pure Chemical Industries, Ltd.), and 0.05 g of niobium oxide (manufactured by Wako Pure Chemical Industries, Ltd.) (20% Ni/SiO$_2$+α-Fe$_2$O$_3$+Nb$_2$O$_5$) was used as the catalyst, and that the temperature in the autoclave was increased to 235° C. and then kept at 235° C. for 3 hours. The results are shown in Table 2.

(Example 14) Production of ε-Caprolactam Using Dimethyl Adipate (I-2) as Material Compound A reaction was carried out in the same manner as in Example 1 except that 0.18 g of dimethyl adipate (manufactured by Tokyo Chemical Industry Co., Ltd.) was used as the material compound, that 50 mL of 1,2-dimethoxyethane (manufactured by Wako Pure Chemical Industries, Ltd.) was used as the solvent, and that a physical mixture of 0.05 g of 10% nickel-supporting silicon dioxide, 0.05 g of α-iron oxide (manufactured by Wako Pure Chemical Industries, Ltd.), and 0.05 g of niobium oxide (manufactured by Wako Pure Chemical Industries, Ltd.) (10% Ni/SiO$_2$+α-Fe$_2$O$_3$+Nb$_2$O$_5$) was used as the catalyst. The results are shown in Table 2.

(Example 15) Production of ε-Caprolactam Using α-Hydromuconic Acid Dimethyl Ester (I-5) as Material Compound A reaction was carried out in the same manner as in Example 4 except that 0.17 g of α-hydromuconic acid dimethyl ester provided in Reference Example 9 was used as the material compound. The results are shown in Table 2.

(Comparative Example 9) Production of ε-Caprolactam Using Diammonium Adipate as Material Compound A reaction was carried out in the same manner as in Example 13 except that 0.1 g of 5% palladium-supporting titanium oxide (5% Pd/TiO$_2$) was used as the catalyst. The results are shown in Table 2.

TABLE 2

Production of ε-caprolactam from various material compounds

| | Material compound | Catalyst | Solvent | Material compound conversion (%) | Intermediate selectivity (%) | By-product selectivity (%) | ε-Caprolactam selectivity (%) |
|---|---|---|---|---|---|---|---|
| Example 1 | Adipic acid | 5% Pd/Nb$_2$O$_5$ | Dioxane | 100 | 5.0 | 2.9 | 82.6 |
| Example 2 | Adipic acid | 5% Ni/Nb$_2$O$_5$ | Dioxane | 100 | 4.9 | 2.3 | 81.4 |
| Example 3 | Adipic acid | 5% Pd/Ta$_2$O$_5$ | Dioxane | 100 | 11.3 | 2.4 | 81.9 |
| Example 4 | t,t-Muconic acid | 5% Pd/Nb$_2$O$_5$ | Dioxane | 100 | 5.2 | 3.2 | 82.8 |
| Example 5 | Adipic acid | 5% Pd/α-Fe$_2$O$_3$ | Dioxane | 100 | 8.1 | 3.9 | 78.0 |
| Example 6 | Adipic acid | 10% Ni/SiO$_2$, α-Fe$_2$O$_3$ | Dioxane | 100 | 2.9 | 2.5 | 83.2 |
| Example 7 | α-Hydromuconic acid | 5% Pd/Nb$_2$O$_5$ | Dioxane | 100 | 13.4 | 2.3 | 76.2 |
| Example 8 | 3-Hydroxyadipic acid | 1.7% Pd/Nb$_2$O$_5$ | Dioxane | 100 | 6.8 | 2.3 | 78.6 |
| Example 10 | Adipic acid | 10% Ni-10%Co/SiO$_2$ + α-Fe$_2$O$_3$ | Dioxane | 100 | 11.8 | 1.2 | 70.5 |
| Example 11 | Adipic acid | 10% Ni-10%Fe/SiO$_2$ + α-Fe$_2$O$_3$ | Dioxane | 100 | 18.0 | 0.8 | 63.7 |
| Example 12 | α-Hydromuconic acid | 10% Ni/SiO$_2$ + α-Fe$_2$O$_3$ | Dioxane | 100 | 10.7 | 3.9 | 73.8 |
| Example 13 | Diammonium adipate | 20% Ni/SiO$_2$ + α-Fe$_2$O$_3$ + Nb$_2$O$_5$ | tert-Butanol | 100 | 1.2 | 4.3 | 83.6 |
| Example 14 | Adipic acid dimethyl ester | 10% Ni/SiO$_2$ + α-Fe$_2$O$_3$ + Nb$_2$O$_5$ | 1,2-dimethoxyethane | 64 | 5.5 | 2.5 | 83.8 |
| Example 15 | α-Hydromuconic acid dimethyl ester | 5% Pd/Nb$_2$O$_5$ | Dioxane | 81 | 7.3 | 2.0 | 77.2 |
| Comparative Example 1 | Adipic acid | 5% Pd/Al$_2$O$_3$ | Dioxane | 100 | 7.8 | 20.1 | 66.4 |
| Comparative Example 2 | Adipic acid | 5% Pd/ZrO$_2$ | Dioxane | 100 | 0.7 | 20.4 | 67.0 |
| Comparative Example 3 | Adipic acid | 5% Pd/TiO$_2$ | Dioxane | 100 | 4.2 | 28.7 | 32.7 |
| Comparative Example 4 | Adipic acid | 5% Pd/SiO$_2$ | Dioxane | 100 | 84.6 | 11.2 | 0.5 |
| Comparative Example 5 | t,t-Muconic acid | 5% Pd/Al$_2$O$_3$ | Dioxane | 100 | 2.7 | 19.9 | 67.6 |
| Comparative Example 6 | α-Hydromuconic acid | 5% Pd/Al$_2$O$_3$ | Dioxane | 100 | 13.7 | 17.9 | 59.1 |
| Comparative Example 7 | 3-Hydroxyadipic acid | 5% Pd/Al$_2$O$_3$ | Dioxane | 100 | 12.3 | 13.2 | 61.1 |
| Comparative Example 9 | Diammonium adipate | 5% Pd/TiO$_2$ | tert-Butanol | 100 | 6.2 | 27.8 | 23.5 |

From the Examples in Table 2, it was shown that a compound from which adipamide can be formed, such as a carboxylic acid represented by General Formula (I) or (II), or a salt or an ester thereof, can be used as a material compound for ε-caprolactam.

(Example 16) Production of 5-Cyanovaleramide from Adipamide

To a stainless steel autoclave having a capacity of 0.1 (manufactured by Taiatsu Techno Corporation), 0.144 g of adipamide (Tokyo Chemical Industry Co., Ltd.), 50 mL of dioxane (Wako Pure Chemical Industries, Ltd.), and 0.1 g of niobium oxide (Nb$_2$O$_5$, manufactured by Wako Pure Chemical Industries, Ltd.) were added. The temperature in the autoclave was adjusted to 30° C., and, with stirring at a stirring rate of 500 rpm, the inside of the autoclave was purged with nitrogen. Ammonia gas was introduced thereto such that the partial pressure of ammonia gas in the autoclave was adjusted to 0.18 MPa (gauge pressure), and then the pressure was kept for 45 minutes. Thereafter, while the stirring was continued, hydrogen was introduced thereto such that the partial pressure of hydrogen in the autoclave was adjusted to 0.72 MPa (gauge pressure) (total pressure (gauge pressure): 0.90 MPa). Subsequently, the temperature in the autoclave was increased to 250° C. After keeping the temperature at 250° C. for 1 hour, the autoclave was allowed to cool to room temperature, and the gas in the autoclave was released to allow the pressure to decrease to ambient pressure, followed by recovering the reaction solution. The catalyst was removed by filtration, and the supernatant was analyzed by GC. The supernatant was concentrated with a rotary evaporator (Tokyo Rikakikai Co., Ltd.). An aqueous solution of the resulting concentrate was prepared, and analyzed by HPLC. The results are shown in Table 3.

Example 17

A reaction was carried out in the same manner as in Example 16 except that tantalum oxide ($Ta_2O_5$, manufactured by Wako Pure Chemical Industries, Ltd.) was used instead of niobium oxide. The results are shown in Table 3.

Example 18

A reaction was carried out in the same manner as in Example 16 except that α-iron oxide (α-$Fe_2O_3$, manufactured by Wako Pure Chemical Industries, Ltd.) was used instead of niobium oxide. The results are shown in Table 3.

Example 19

A reaction was carried out in the same manner as in Example 16 except that zinc oxide (ZnO, manufactured by Wako Pure Chemical Industries, Ltd.) was used instead of niobium oxide. The results are shown in Table 3.

Example 20

A reaction was carried out in the same manner as in Example 16 except that indium oxide ($In_2O_3$, manufactured by Wako Pure Chemical Industries, Ltd.) was used instead of niobium oxide. The results are shown in Table 3.

Example 21

A reaction was carried out in the same manner as in Example 16 except that tin oxide ($SnO_2$, manufactured by Wako Pure Chemical Industries, Ltd.) was used instead of niobium oxide. The results are shown in Table 3.

Example 22

A reaction was carried out in the same manner as in Example 16 except that lead oxide (PbO, manufactured by Wako Pure Chemical Industries, Ltd.) was used instead of niobium oxide. The results are shown in Table 3.

Example 23

A reaction was carried out in the same manner as in Example 16 except that 20% indium oxide-supporting silicon dioxide (20% $In_2O_3/SiO_2$) prepared in Reference Example 5 was used instead of niobium oxide. The results are shown in Table 3.

Comparative Example 10

A reaction was carried out in the same manner as in Example 16 except that Aluminium oxide, gamma-phase ($Al_2O_3$, manufactured by Alfa Aesar) was used instead of niobium oxide. The results are shown in Table 3.

Comparative Example 11

A reaction was carried out in the same manner as in Example 16 except that zirconium oxide ($ZrO_2$, reference catalyst JRC—ZRO-3 according to Catalysis Society of Japan) was used instead of niobium oxide. The results are shown in Table 3.

Comparative Example 12

A reaction was carried out in the same manner as in Example 16 except that silicon dioxide ($SiO_2$, CARiACT G6, manufactured by Fuji Silysia Chemical Ltd.) was used instead of niobium oxide. The results are shown in Table 3.

Comparative Example 13

A reaction was carried out in the same manner as in Example 16 except that magnesium oxide (MgO, reference catalyst JRC-MGO-3-1000A according to Catalysis Society of Japan) was used instead of niobium oxide. The results are shown in Table 3.

Comparative Example 14

A reaction was carried out in the same manner as in Example 16 except that scandium oxide ($Sc_2O_3$, manufactured by Mitsuwa Chemicals Co., Ltd.) was used instead of niobium oxide. The results are shown in Table 3.

Comparative Example 15

A reaction was carried out in the same manner as in Example 16 except that cerium oxide ($CeO_2$, reference catalyst JRC-CEO-3 according to Catalysis Society of Japan) was used instead of niobium oxide. The results are shown in Table 3.

Comparative Example 16

A reaction was carried out in the same manner as in Example 16 except that antimony oxide ($Sb_2O_3$, manufactured by Wako Pure Chemical Industries, Ltd.) was used instead of niobium oxide. The results are shown in Table 3.

Comparative Example 17

A reaction was carried out in the same manner as in Example 16 except that bismuth oxide ($Bi_2O_3$, manufactured by Wako Pure Chemical Industries, Ltd.) was used instead of niobium oxide. The results are shown in Table 3.

Example 24

A reaction was carried out in the same manner as in Example 16 except that triiron tetroxide ($Fe_3O_4$, manufactured by Wako Pure Chemical Industries, Ltd.) was used instead of niobium oxide. The results are shown in Table 3.

Example 25

A reaction was carried out in the same manner as in Example 16 except that manganese dioxide ($MnO_2$, manufactured by Wako Pure Chemical Industries, Ltd.) was used instead of niobium oxide. The results are shown in Table 3.

Example 26

The reaction was carried out in the same manner as in Example 18 except that the temperature in the autoclave was set to 230° C., and that the temperature of 230° C. was kept for 1 hour.

Example 27

A reaction was carried out in the same manner as in Example 16 except that a physical mixture of 0.1 g of α-iron oxide (manufactured by Wako Pure Chemical Industries, Ltd.) and 0.1 g of silicon dioxide (CARiACT G6, manufactured by Fuji Silysia Chemical Ltd.) (α-$Fe_2O_3$+ $SiO_2$) was used instead of niobium oxide. The results are shown in Table 3.

TABLE 3

Production of 5-cyanovaleramide from adipamide

| | Metal oxide | Selectivity of 5-Cyano-valeramide (%) | Selectivity of Adi-ponitrile (%) | By-product precursor selectivity (%) |
|---|---|---|---|---|
| Example 16 | $Nb_2O_5$ | 70.7 | 14.8 | 0.9 |
| Example 17 | $Ta_2O_5$ | 82.5 | 5.5 | 1.9 |
| Example 18 | α-$Fe_2O_3$ | 75.0 | 7.2 | 1.4 |
| Example 19 | ZnO | 85.9 | 1.0 | 5.8 |
| Example 20 | $In_2O_3$ | 80.7 | 8.3 | 0.9 |
| Example 21 | $SnO_2$ | 71.7 | 2.3 | 3.1 |
| Example 22 | PbO | 71.8 | 1.7 | 11.8 |
| Example 23 | 20% $In_2O_3$/ $SiO_2$ | 75.0 | 4.0 | 4.4 |
| Example 24 | $Fe_3O_4$ | 70.5 | 1.2 | 12.0 |
| Example 25 | $MnO_2$ | 68.8 | 2.6 | 9.1 |
| Example 26 | α-$Fe_2O_3$ | 82.7 | 3.4 | 4.0 |
| Example 27 | α-$Fe_2O_3$ + $SiO_2$ | 75.3 | 10.2 | 2.5 |
| Comparative Example 10 | $Al_2O_3$ | 47.4 | 3.1 | 23.1 |
| Comparative Example 11 | $ZrO_2$ | 39.1 | 17.2 | 14.4 |
| Comparative Example 12 | $SiO_2$ | 29.7 | Not detected | 8.7 |
| Comparative Example 13 | MgO | 16.5 | Not detected | 45.9 |
| Comparative Example 14 | $Sc_2O_3$ | 35.0 | Not detected | 5.1 |
| Comparative Example 15 | $CeO_2$ | 2.3 | 12.3 | 43.1 |
| Comparative Example 16 | $Sb_2O_3$ | 11.3 | Not detected | 4.0 |
| Comparative Example 17 | $Bi_2O_3$ | 38.5 | Not detected | Not detected |

From the results of the Examples shown in Table 3, it was shown that, in cases where a metal oxide mainly containing an oxide of a metallic element in group 5 or groups 7 to 14 in the 4th to 6th periods of the periodic table is used to perform a reaction to convert adipamide to 5-cyanovaleramide, formation of by-product precursors that do not contribute to formation of s-caprolactam can be suppressed, leading to a high selectivity of 5-cyanovaleramide. Furthermore, from the results of the Examples shown in Table 2, it was shown that, in cases where a catalyst containing: a metal oxide mainly containing an oxide of a metallic element in group 5 or groups 7 to 14 in the 4th to 6th periods of the periodic table, such as a metal oxide used in the Examples shown in Table 3; and a metal and/or a metal compound having a hydrogenation ability; is used, the selectivities of by-products that do not contribute to formation of s-caprolactam are low, and the ε-caprolactam selectivity is high.

On the other hand, from the results of the Comparative Examples shown in Table 3, it was shown that, in cases where a metal oxide mainly containing an oxide of a metallic element other than the metallic elements of group 5 and groups 7 to 14 in the 4th to 6th periods of the periodic table is used alone to perform a reaction to convert adipamide to 5-cyanovaleramide, the selectivity of 5-cyanovaleramide is low, or large amounts of precursors of by-products that do not contribute to formation of ε-caprolactam are formed. Furthermore, from the results of the Comparative Examples shown in Table 2, it was shown that, in cases where a catalyst containing: a metal oxide mainly containing an oxide of a metallic element other than the metallic elements of group 5 and groups 7 to 14 in the 4th to 6th periods of the periodic table, such as a metal oxide used in the Comparative Examples shown in Table 3; and a metal and/or a metal compound having a hydrogenation ability; is used, the selectivities of by-products that do not contribute to formation of ε-caprolactam are high, and the ε-caprolactam selectivity is insufficient.

As described above, it was shown that, in the method of producing 8-caprolactam using adipamide as an intermediate, by reacting adipamide, formed from a material compound, with hydrogen and ammonia in the presence of a catalyst containing: a metal oxide mainly containing an oxide(s) of one or more metallic elements selected from the group consisting of metallic elements of group 5 and groups 7 to 14 in the 4th to 6th periods of the periodic table; and a metal and/or a metal compound having a hydrogenation ability; side reactions from adipamide can be suppressed well, and the ε-caprolactam selectivity can be increased.

The invention claimed is:

1. A method of producing 5-cyanovaleramide through adipamide as an intermediate, the method comprising converting adipamide, formed from a material compound, to 5-cyanovaleramide in the presence of a metal oxide and a solvent, wherein the metal oxide an oxide of one or more metallic elements selected from the group consisting of metallic elements of group 5 and groups 7 to 14 in the 4th to 6th periods of the periodic table, wherein said material compound is a carboxylic acid represented by the following Formula (I) or (II):

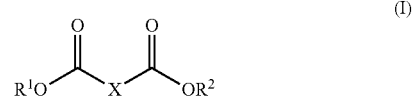

(I)

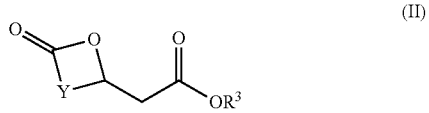

(II)

wherein in Formula (I) and Formula (II), R', $R^2$, and $R^3$ each independently represent a hydrogen atom (H) or an alkyl group having 1 to 6 carbon atoms;

in Formula (I), X represents —$CH_2$—$CH_2$—$CH_2$—$CH_2$—, —$CH_2$—$CH_2$—CH=CH—, —$CH_2$—CH=CH—$CH_2$—, —CH=CH—CH=CH—, —$CH_2$—$CH_2$—$CH_2$—CH(OH)—, —$CH_2$—$CH_2$—C(OH)H—$CH_2$—, —CH=CH—C(OH)H—$CH_2$—, —C(OH)H—CH₂—CH=CH—, or —CH₂—CH=CH—CH(OH)—; and, in Formula (II), Y represents —CH₂—CH₂— or —CH=CH—, or a salt or an ester thereof, or a mixture thereof; and wherein said oxide of one or more metallic elements constitutes only said oxide of said metallic element, or said oxide of one or more metallic elements is in the form of a composite metal oxide in which the oxide of said metallic element covers the surface of an oxide of a metallic element other than said metallic element wherein the ratio of said oxide of said metallic element in said composite metal oxide is 2% by weight to 80% by weight.

2. The method according to claim 1, wherein the material compound is one or more compounds selected from the following group of compounds:

(I-1)
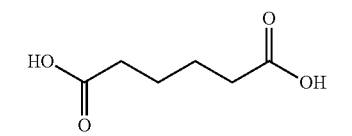

(I-2)
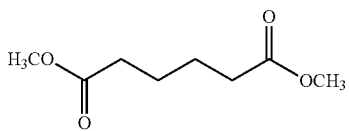

(I-3)
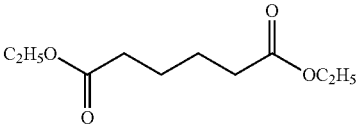

(I-4)
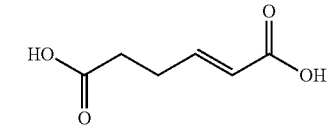

(I-5)
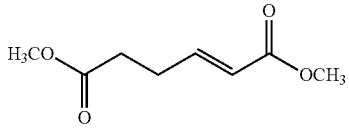

(I-6)
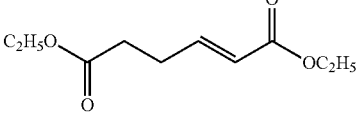

(I-7)
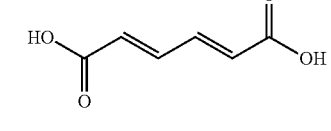

(I-8)
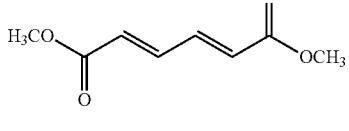

-continued (I-9)
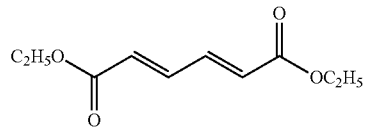

(I-10)
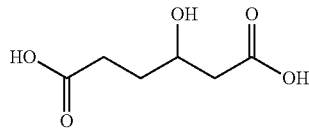

(I-11)
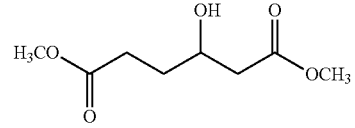

(I-12)
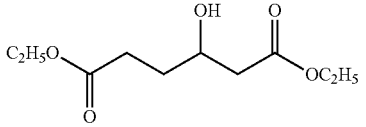

(II-1)
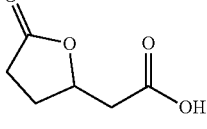

(II-2)
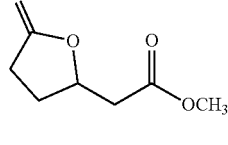

(II-3)
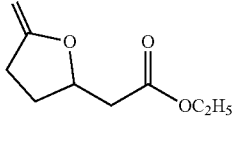

(II-4)
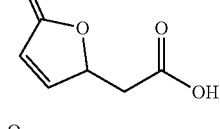

(II-5)
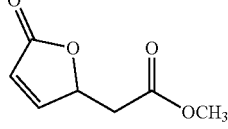

(II-6)
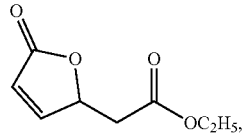

or a salt(s) thereof, or a mixture thereof.

3. The method according to claim 1, wherein the material compound is one or more carboxylic acids selected from the group consisting of adipic acid, muconic acid, 3-hydroxyadipic acid, α-hydromuconic acid, 3-hydroxyadipic acid-3,6-lactone, and muconolactone, or a salt(s) thereof, or a mixture thereof.

4. The method according to claim 1, wherein the oxide of the metallic element is an oxide of one or more metallic elements selected from the group consisting of vanadium, niobium, tantalum, manganese, iron, cobalt, nickel, copper, zinc, gallium, indium, thorium, germanium, tin, and lead.

* * * * *